(12) United States Patent
Kasahara et al.

(10) Patent No.: US 10,054,432 B2
(45) Date of Patent: Aug. 21, 2018

(54) X-RAY INSPECTION APPARATUS AND CONTROL METHOD

(71) Applicant: OMRON Corporation, Kyoto-shi, Kyoto (JP)

(72) Inventors: Hironori Kasahara, Otsu (JP); Shinji Sugita, Kyoto (JP); Takako Onishi, Kyotanabe (JP)

(73) Assignee: OMRON Corporation, Kyoto-shi (JP)

( * ) Notice: Subject to any disclaimer, the term of this patent is extended or adjusted under 35 U.S.C. 154(b) by 0 days.

(21) Appl. No.: 15/685,031

(22) Filed: Aug. 24, 2017

(65) Prior Publication Data
US 2018/0080763 A1   Mar. 22, 2018

(30) Foreign Application Priority Data

Sep. 20, 2016   (JP) ................................ 2016-182825

(51) Int. Cl.
| | | |
|---|---|---|
| G01B 11/00 | (2006.01) | |
| G01B 11/25 | (2006.01) | |
| H04N 13/282 | (2018.01) | |
| G06T 7/55 | (2017.01) | |
| G01N 23/083 | (2018.01) | |

(Continued)

(52) U.S. Cl.
CPC ....... *G01B 11/2527* (2013.01); *G01N 23/046* (2013.01); *G01N 23/083* (2013.01); *G01N 23/18* (2013.01); *G01N 23/223* (2013.01); *G01S 15/8925* (2013.01); *G06T 7/0002* (2013.01); *G06T 7/55* (2017.01); *H04N 13/0282* (2013.01); *H04N 13/282* (2018.05);

(Continued)

(58) Field of Classification Search
CPC ...... G01B 11/2527; G06T 7/55; H04N 13/282
See application file for complete search history.

(56) References Cited

U.S. PATENT DOCUMENTS

| | | | |
|---|---|---|---|
| 5,594,768 A | 1/1997 | Fujii et al. | |
| 2005/0041781 A1* | 2/2005 | Jefferson | G06T 11/006 378/210 |

(Continued)

FOREIGN PATENT DOCUMENTS

| | | |
|---|---|---|
| EP | 2778662 A1 | 9/2014 |
| JP | H07-221151 A | 8/1995 |
| JP | 2010-145359 A | 7/2010 |

OTHER PUBLICATIONS

The extended European search report (EESR) dated Dec. 20, 2017 in a counterpart European Patent application.

*Primary Examiner* — Hugh H Maupin
(74) *Attorney, Agent, or Firm* — Metrolexis Law Group, PLLC

(57) ABSTRACT

An X-ray inspection apparatus includes a 3D processing unit that performs 3D imaging of a first area in an inspection area, a 2D processing unit that performs 2D imaging of a second area in the inspection area, an extraction unit that extracts 3D information for a first inspection target from a 3D image of the first area, and 2D information for a second inspection target from a 2D image of the second area, a 3D information estimation unit that estimates 3D information for the second inspection target using the extracted 3D information for the first inspection target, and an inspection unit that inspects the second inspection target using the 2D information for the second inspection target and the estimated 3D information for the second inspection target.

15 Claims, 17 Drawing Sheets

(51) Int. Cl.
*G01N 23/18* (2018.01)
*G01N 23/223* (2006.01)
*G01S 15/89* (2006.01)
*G06T 7/00* (2017.01)
*H04N 13/02* (2006.01)
*G01N 23/046* (2018.01)

(52) U.S. Cl.
CPC .. *G01N 2223/611* (2013.01); *G01N 2223/645* (2013.01); *G01N 2223/646* (2013.01)

(56) References Cited

U.S. PATENT DOCUMENTS

2008/0266825 A1 10/2008 Tokii
2010/0034452 A1* 2/2010 Gines .................... G06T 7/0006
382/132

* cited by examiner

FIG. 2A
3D imaging areas
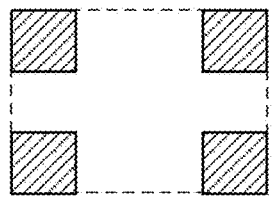
2D imaging areas
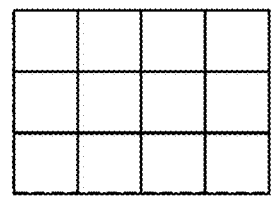
FIG. 2B
3D imaging areas
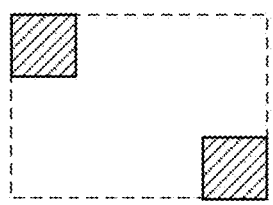
2D imaging areas
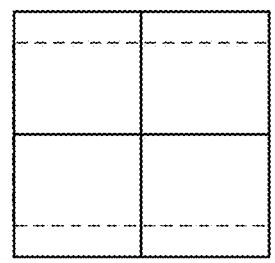
FIG. 2C
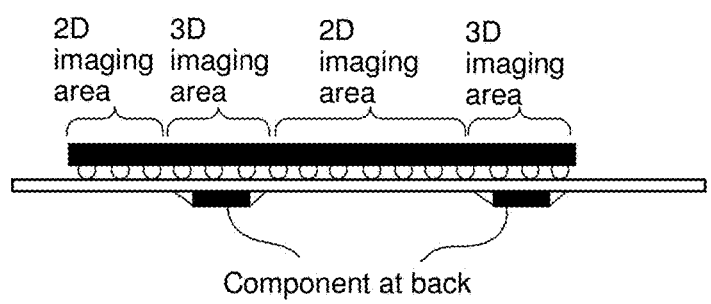
Component at back

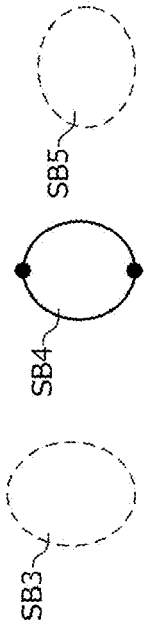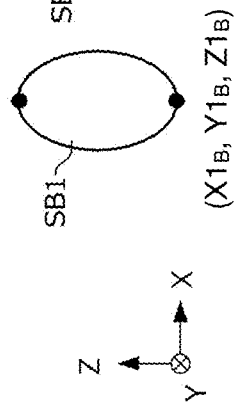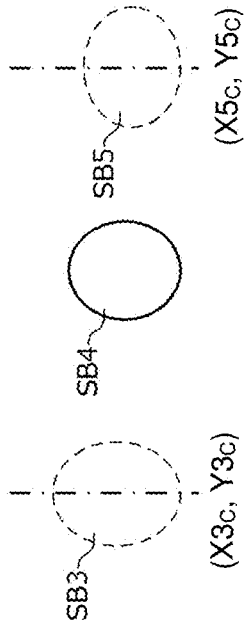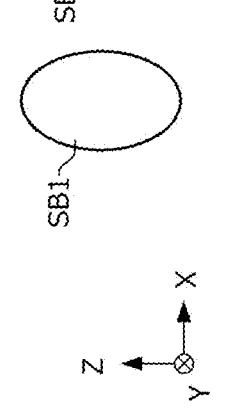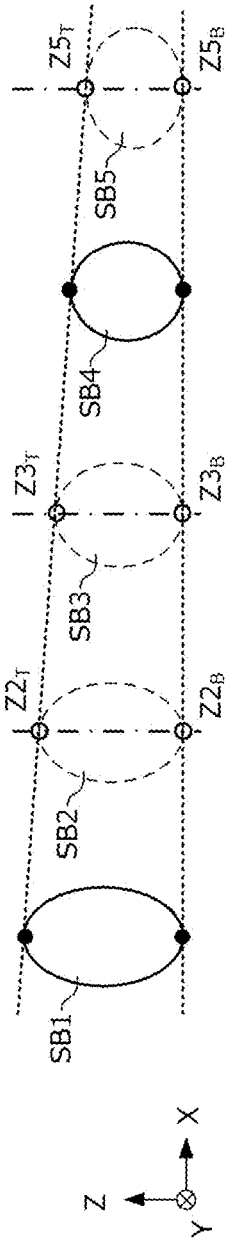
FIG. 9A  FIG. 9B  FIG. 9C

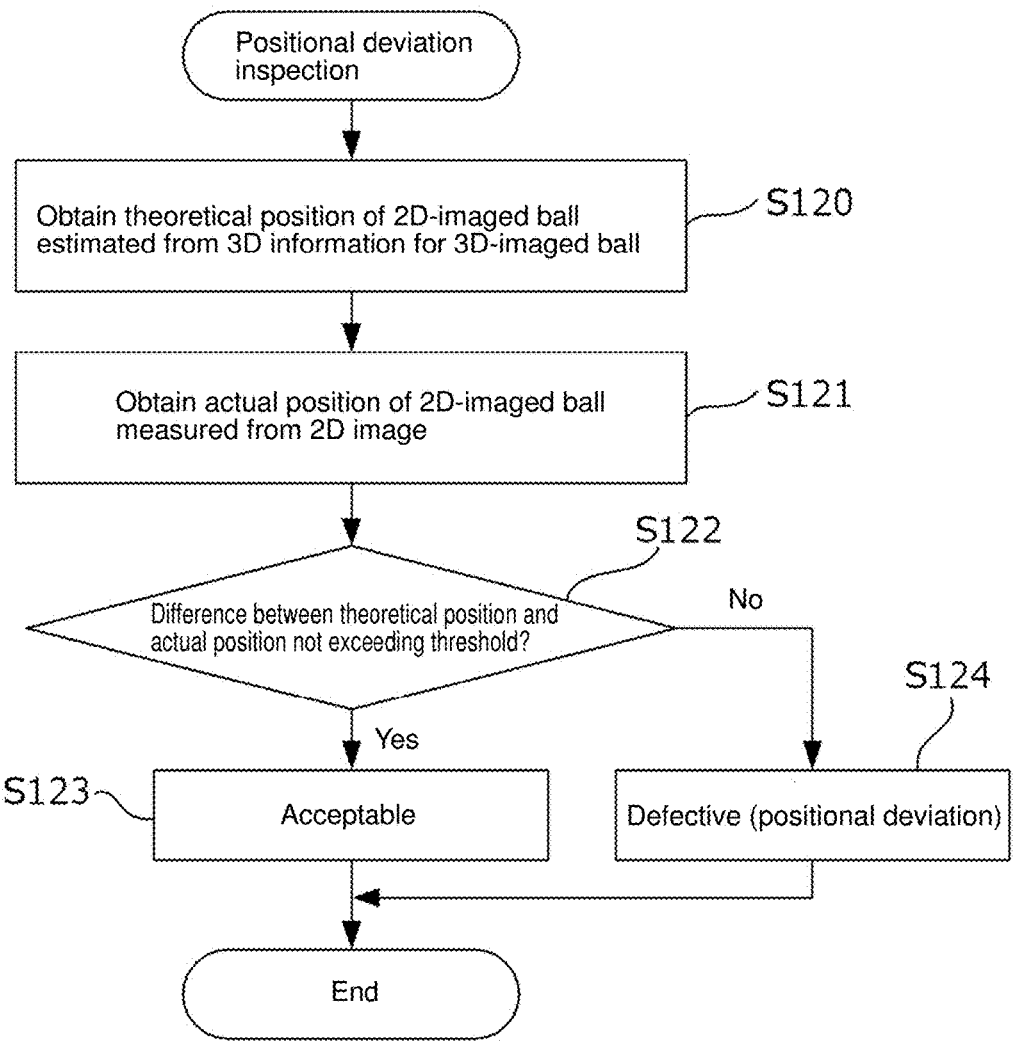

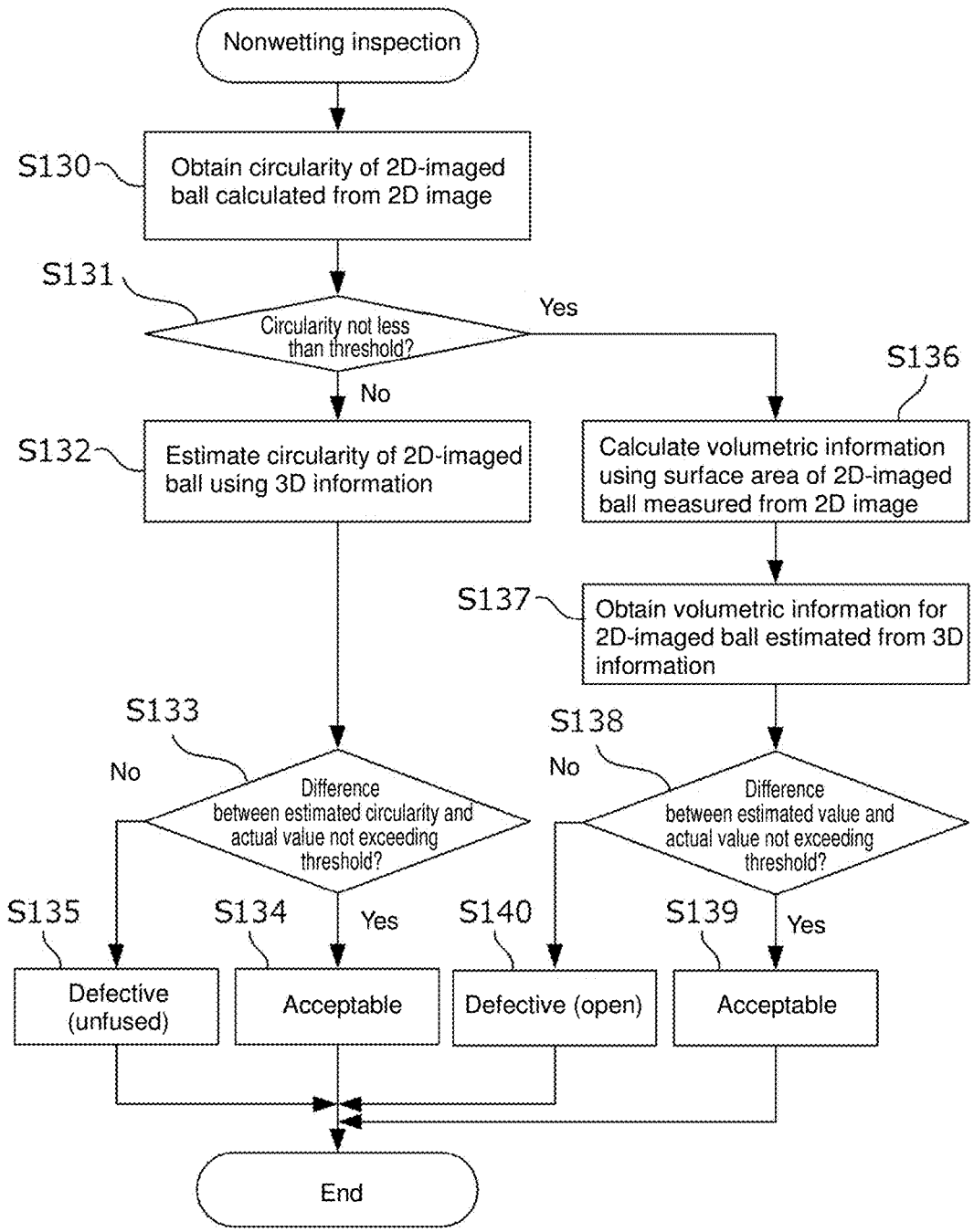

Ball diameter: 300 μm

1 FOV
(20 μm resolution)

2000 pix = 40 mm 2000 pix = 40 mm

Ball diameter: 80 μm

30 FOVs
(3 μm resolution)

2000 pix = 6 mm 2000 pix = 6 mm

US 10,054,432 B2

X-RAY INSPECTION APPARATUS AND CONTROL METHOD

CROSS REFERENCE TO RELATED APPLICATIONS

This application claims priority from prior Japanese Patent Application No. 2013-182825 filed with the Japan Patent Office on Sep. 20, 2016, the entire contents of which are incorporated herein by reference.

FIELD

The disclosure relates to an industrial X-ray inspection apparatus.

BACKGROUND

Industrial X-ray inspection apparatuses known in the art may use image information obtained through X-ray imaging to detect defects or faults in industrial products. Such X-ray inspection apparatuses can inspect parts of a workpiece not easily viewable in the appearance or the internal state of a workpiece in a nondestructive manner, and are used in, for example, inspecting the state of solder joints on components mounted on a surface mounting board.

Imaging techniques used in X-ray inspection are mainly 2D imaging or 3D imaging. In 2D imaging, X-rays are applied to an inspection workpiece in one direction, and the resulting transmission image is obtained as 2D image information. In 3D imaging, multiple transmission images are captured by changing the direction in which X-rays are applied. Using the obtained images, 3D image information for an inspection workpiece, such as 3D volume data or a tomographic image at a given section of the object, is obtained. Computed tomography (CT) and tomosynthesis are typically known as such 3D imaging techniques. The inspection using 2D image information obtained from 2D images is herein referred to as 2D inspection. The inspection using 3D image information obtained from 3D images is referred to as 3D inspection.

As shown in FIG. 16A, a ball grid array (BGA) component may have, for example, a defective state in which a gap forms between a solder ball 162 on a component 160 and a solder paste piece 163 on a circuit board 161 (open), or a defective state in which a solder ball 162 is not fused with a solder paste piece 163 (unfused or head in pillow). However, as shown in FIG. 16B, solder balls 162 and solder paste pieces 163 cannot be easily distinguished in the transmission image obtained through 2D imaging. Distinguishing components in defective states from non-defective components is thus difficult. As a result, 2D inspection can allow such defective components to pass the inspection due to false negatives, or can lower the first pass yield due to false positives. For such defects that are difficult to detect by 2D inspection, 3D inspection may be used. For example, Patent Literature 1 describes a technique for inspecting solder balls in a BGA component with high accuracy using tomographic images obtained through tomosynthesis.

CITATION LIST

Patent Literature

Patent Literature 1: Japanese Unexamined Patent Application Publication No. 7-221151

SUMMARY

Technical Problem

As described above, 3D inspection is effective for defects that are difficult to detect using 2D transmission images alone. However, 3D inspection has issues described below.

A first issue is the time taken for imaging and inspection. Whereas 2D inspection involves a single imaging process for capturing a transmission image for a single field of view (FOV), 3D inspection involves imaging performed several to several tens of times to capture images for a single field of view. Thus, 3D inspection takes more imaging time than 2D imaging. This lowers the inspection throughput. This issue is more serious for recent component packages that are smaller and denser. Imaging is to be performed with a higher resolution for solder balls with a smaller diameter or a narrower pitch. In this case, a single component may need to be captured using multiple fields of view. The imaging time increases in proportion to the number of fields of view. As shown in FIG. 17A, imaging using a single field of view (with a FOV size of 40×40 mm) is performed for a BGA component including solder balls with a diameter of 300 μm with a detector having 2000×2000 pixels with a resolution of 20 μm. For a BGA component including solder balls with a diameter of 80 μm captured using the same detector with a resolution of 3 μm, the imaging process uses 30 fields of view (with a FOV size of 6×6 mm) as shown in FIG. 17B.

A second issue is radiation exposure of components. Exposure to an amount of radiation that exceeds the permissible limit can degrade the performance of electronic components or can cause faults. Thus, the number of imaging processes (the number of X-ray irradiations) is to be minimized.

In response to the above issues, one or more aspects are directed to a technique enabling inspection with less time and less radiation exposure for defects that are difficult to detect using 2D transmission images alone.

Solution to Problem

In response to the above issues, an apparatus and a method according to one or more aspects allow inspection using 2D imaging information and 3D imaging information in combination.

More specifically, one or more aspects may provide an X-ray inspection apparatus for inspecting a workpiece including a plurality of inspection targets. The apparatus includes a 3D processing unit, a 2D processing unit, an extraction unit, a 3D information estimation unit, and an inspection unit. The 3D processing unit performs 3D imaging for capturing a 3D image of a first area through multiple X-ray irradiations. The first area is a part of an inspection area defined for the workpiece. The 2D processing unit performs 2D imaging for capturing a 2D image of a second area through a single X-ray irradiation. The second area is a part of the inspection area and is different from the first area. The extraction unit extracts 3D information for a first inspection target included in the first area from the 3D image of the first area captured through the 3D imaging, and extracts 2D information for a second inspection target included in the second area from the 2D image of the second area captured through the 2D imaging. The 3D information estimation unit estimates 3D information for the second inspection target using the 3D information for the first inspection target extracted by the extraction unit. The inspection unit inspects the second inspection target using the 2D information for the second inspection target extracted by the extraction unit and the 3D information for the second inspection target estimated by the 3D information estimation unit.

In this structure, the inspection uses 3D imaging in a limited portion of the inspection area (the first area only), and thus uses fewer imaging processes and fewer X-ray irradiations, and shortens the imaging time and the inspection time, as well as reduces the amount of radiation exposure, unlike when performing 3D imaging of the entire inspection area. The inspection may estimate 3D information for any second inspection target included in the second area using the 3D information extracted from the 3D images of the first area. Using the estimated 3D information in the inspection of the second inspection target, pseudo 3D inspection can be performed for the second inspection target that has undergone 2D imaging alone. This allows inspection for defects that are difficult to detect in 2D inspection.

The 2D information is geometric information in the 2D-space (2D-plane), and includes, for example, the position, size, width, distance, surface area, and shape in the 2D-plane. The 3D information is geometric information in the 3D-space, and includes, for example, the position, size, height, distance, sectional area, volume, and shape in the 3D-space.

The 3D information may be estimated using any method. When the first area includes a plurality of inspection targets, for example, the 3D information estimation unit may calculate the 3D information for the second inspection target through interpolation or extrapolation using the 3D information for the plurality of first inspection targets.

An XYZ coordinate system is defined to have an XY-plane orthogonal to a direction of X-ray irradiation in the 2D imaging, and the workpiece has a first end and a second end in Z-direction.

For example, the extraction unit may extract an XY-position and a Z-direction height of each of the plurality of first inspection targets from the 3D image of the first area, and extract an XY-position of the second inspection target from the 2D image of the second area. The 3D information estimation unit may calculate a Z-direction height of the second inspection target at the XY-position through interpolation or extrapolation using the Z-direction height of each of the plurality of first inspection targets. This allows pseudo 3D inspection using the estimated Z-direction height to be performed for the second inspection target.

The extraction unit may extract an XY-position and volumetric information of each of the plurality of first inspection targets from the 3D image of the first area, and extract an XY-position of the second inspection target from the 2D image of the second area. The 3D information estimation unit may calculate volumetric information of the second inspection target at the XY-position through interpolation or extrapolation using the volumetric information of each of the plurality of first inspection targets. This allows pseudo 3D inspection using the estimated volumetric information to be performed for the second inspection target.

The extraction unit may extract an XY-position of each of the plurality of first inspection targets from the 3D image of the first area. The 3D information estimation unit may calculate a predicted XY-position of the second inspection target through interpolation or extrapolation using the XY-position of each of the plurality of first inspection targets.

The predicted XY-position (hereafter, the theoretical position) of the second inspection target may be obtained from, for example, CAD information of the workpiece. However, when the workpiece has manufacturing errors or positional deviations across the entire workpiece, the actual position of the second inspection target may deviate from the obtained CAD information. In this case, when the second inspection target is inspected using the theoretical position obtained from the CAD information as a reference (correct) position, the inspection cannot yield a reliable result.

In one or more aspects, the theoretical position of the second inspection target is estimated using the XY-position (relative positional relationship) of the first inspection target obtained through the 3D imaging. This can yield the theoretical position of the second inspection that reflects the actual state of the workpiece (e.g., manufacturing errors or positional deviations across the entire workpiece). The inspection for the second inspection target using such theoretical positions can yield more reliable inspection results, thus improving the inspection accuracy and reliability.

The extraction unit may extract XYZ-positions of a first end and a second end of each of the plurality of first inspection targets from the 3D image of the first area. The 3D information estimation unit may calculate a predicted XYZ-position of a first end of the second inspection target through interpolation or extrapolation using the XYZ-position of the first end of each of the plurality of first inspection targets, and calculate a predicted XYZ-position of the second end of the second inspection target through interpolation or extrapolation using the XYZ-position of the second end of each of the plurality of the first inspection targets.

This structure can yield the theoretical positions of both ends of the second inspection that reflect the actual state of the workpiece (e.g., manufacturing errors or positional deviations across the entire workpiece). The inspection for the second inspection target using such theoretical positions can yield more reliable inspection results, thus improving the inspection accuracy and reliability.

The 3D information estimation unit may calculate a deviation between the first end and the second end of the second inspection target in the XY-plane using the predicted XYZ-position of the first end and the predicted XYZ-position of the second end. The 3D information estimation unit may also calculate a predicted XY-positon of the second inspection target by calculating an average of the predicted XYZ-position of the first end and the predicted XYZ-position of the second end.

This structure can yield the theoretical positions of the second inspection that reflect the actual state of the workpiece (e.g., manufacturing errors or positional deviations across the entire workpiece). The inspection for the second inspection target using such theoretical positions can yield more reliable inspection results, thus improving the inspection accuracy and reliability.

For example, the extraction unit may extract an actual XY-position of the second inspection target from the 2D image of the second area. The inspection unit may compare the actual XY-position of the second inspection target extracted by the extraction unit with the predicted XY-position of the second inspection target estimated by the 3D information estimation unit to determine whether the second inspection target is defective.

This structure can yield reliable inspection results reflecting the actual state of the workpiece (e.g., manufacturing errors or positional deviations across the entire workpiece) by comparing the theoretical position of the second inspection target estimated from the 3D imaging result with the actual position of the second inspection target calculated from the 2D imaging result, thus improving the inspection accuracy and reliability.

The extraction unit may extract a distance between the second inspection target and an inspection target adjacent to the second inspection target from the 2D image of the second area. The inspection unit may determine whether the second inspection target is defective using the distance extracted by the extraction unit and the deviation between the first end and the second end of the second inspection target in the XY-plane estimated by the 3D information estimation unit.

When the second inspection target tilts more relative to the Z-axis, the projected image of the second inspection target becomes larger, because the second inspection target is projected in the XY-plane as a 2D image. The appearance distance (interval) between the second inspection target and the adjacent inspection target will thus be smaller in the 2D image. The index to be evaluated in the inspection is not the appearance distance between projected images but is the actual 3D distance. However, the 3D distance cannot be determined using the 2D image alone. Thus, the inspection according to one or more aspects reflects the deviation between the first end and the second end of the second inspection target in the XY-plane estimated from the 3D imaging result. The deviation is an index correlated with a tilt relative to the Z-axis. The method according to one or more aspects can thus yield reliable inspection results reflecting the tilt of the second target inspection, thus improving the inspection accuracy and reliability.

The extraction unit may extract an actual circularity of the second inspection target from the 2D image of the second area. The inspection unit may estimate a circularity of the second inspection target using the deviation between the first end and the second end of the second inspection target in the XY-plane, and compare the estimated circularity with the actual circularity of the second inspection target extracted by the extraction unit to determine whether the second inspection target is defective.

When the second inspection target tilts more relative to the Z-axis, the circularity deviates more, because the second inspection target is projected in the XY-plane as a 2D image. Focusing on such characteristics, the inspection described above can allow the inspection for defects that cannot be detected using 2D inspection alone, by comparing the theoretical circularity of the second inspection target estimated from the 3D imaging result with the actual circularity of the second inspection target calculated from the 2D imaging result.

The extraction unit may extract an XY-position, a Z-direction height, and volumetric information of each of the plurality of first inspection targets from the 3D image of the first area, and extract an XY-position and a surface area of the second inspection target from the 2D image of the second area. The 3D information estimation unit may calculate a Z-direction height and volumetric information of the second inspection target at the XY-position through interpolation or extrapolation using the Z-direction height and the volumetric information of each of the plurality of first inspection targets. The inspection unit may compare the volumetric information of the second inspection target calculated from the surface area of the second inspection target extracted by the extraction unit and the Z-direction height of the second inspection target estimated by the 3D information estimation unit with the volumetric information of the second inspection target estimated by the 3D information estimation unit to determine whether the second inspection target is defective.

This structure can allow the inspection for defects that cannot be detected using 2D inspection alone, by comparing the volumetric information of the second inspection target estimated from the 2D imaging result with the volumetric information of the second inspection target estimated from the 3D imaging result.

The workpiece may be an electronic component, and each inspection target may be a solder piece for joining the electronic component and a circuit board. For example, the inspection according to one or more aspects is useful for inspecting an electronic component such as a BGA that includes multiple solder pieces with substantially the same size and the same shape and arranged in a regular pattern.

One or more aspects provide an X-ray inspection apparatus including at least some of the components or functions described above. One or more aspects also provide a method for controlling the X-ray inspection apparatus including at least some of the processes or an X-ray inspection method. One or more aspects also provide a program enabling a processor of the X-ray inspection apparatus or a computer to implement the processes included in the method, or a computer-readable storage medium storing the program in a non-transitory manner. The components and processes described above may be combined when such combinations do not cause technical conflicts between them.

Advantageous Effects

One or more aspects may enable inspection with less time and less radiation exposure for defects that are difficult to detect using 2D transmission images alone.

BRIEF DESCRIPTION OF THE DRAWINGS

FIGS. 2A to 2C are diagrams illustrating various patterns of field of view assignment.

FIGS. 9A to 9C are diagrams illustrating a method for approximate calculation of the height of a 2D-imaged ball in Z-direction.

FIG. 12 is a flowchart illustrating a positional deviation inspection process for a 2D-imaged ball.

FIG. 13 is a flowchart illustrating a nonwetting inspection process for a 2D-imaged ball.

DETAILED DESCRIPTION

The disclosure relates to an X-ray inspection apparatus, and more particularly, to an X-ray inspection apparatus for inspecting the three-dimensional (3D) shape of an inspection workpiece including a plurality of inspection targets. Although the apparatus may be used for any inspection workpiece, the apparatus may be useful for an inspection workpiece including a plurality of inspection targets arranged in a regular pattern and having a large size and the inspection area cannot be captured in a single shot (the inspection area is to be divided into multiple areas for imaging).

An X-ray inspection apparatus for inspecting a solder joint between an electronic component and a surface mounting board will now be described as one application example. In the X-ray circuit board inspection apparatus, the inspection workpiece is an electronic component (hereafter simply, a component), and the inspection target is a solder piece for joining the electronic component and a circuit board. For example, a component such as a ball grid array (BGA) includes solder pieces hidden under the component and not visible, and thus cannot be inspected through appearance inspection using a visible light camera. A component such as a BGA includes solder balls with substantially the same size and the same shape and arranged in a regular pattern. This type of component can be inspected with the apparatus according to the present embodiment.

2D/3D-combined Inspection

A 2D/3D-combined inspection characteristic of the X-ray inspection apparatus according to the present embodiment will now be described.

As described in the Background section, 2D inspection involves fewer imaging processes and thus takes less inspection time, but may not detect certain types of defects. In contrast, 3D inspection allows more accurate inspection than 2D inspection, but involves far more imaging processes than 2D inspection and thus takes far more inspection time.

The inspection according to the present embodiment uses 3D imaging partly in the inspection area, and uses 2D imaging in the remaining inspection area. Based on 3D information obtained from the partial area is then used to estimate 3D information for the remaining area. The estimated 3D information is then used to perform a pseudo 3D inspection. This inspection method is herein referred to as 2D/3D-combined inspection.

Figure 1:
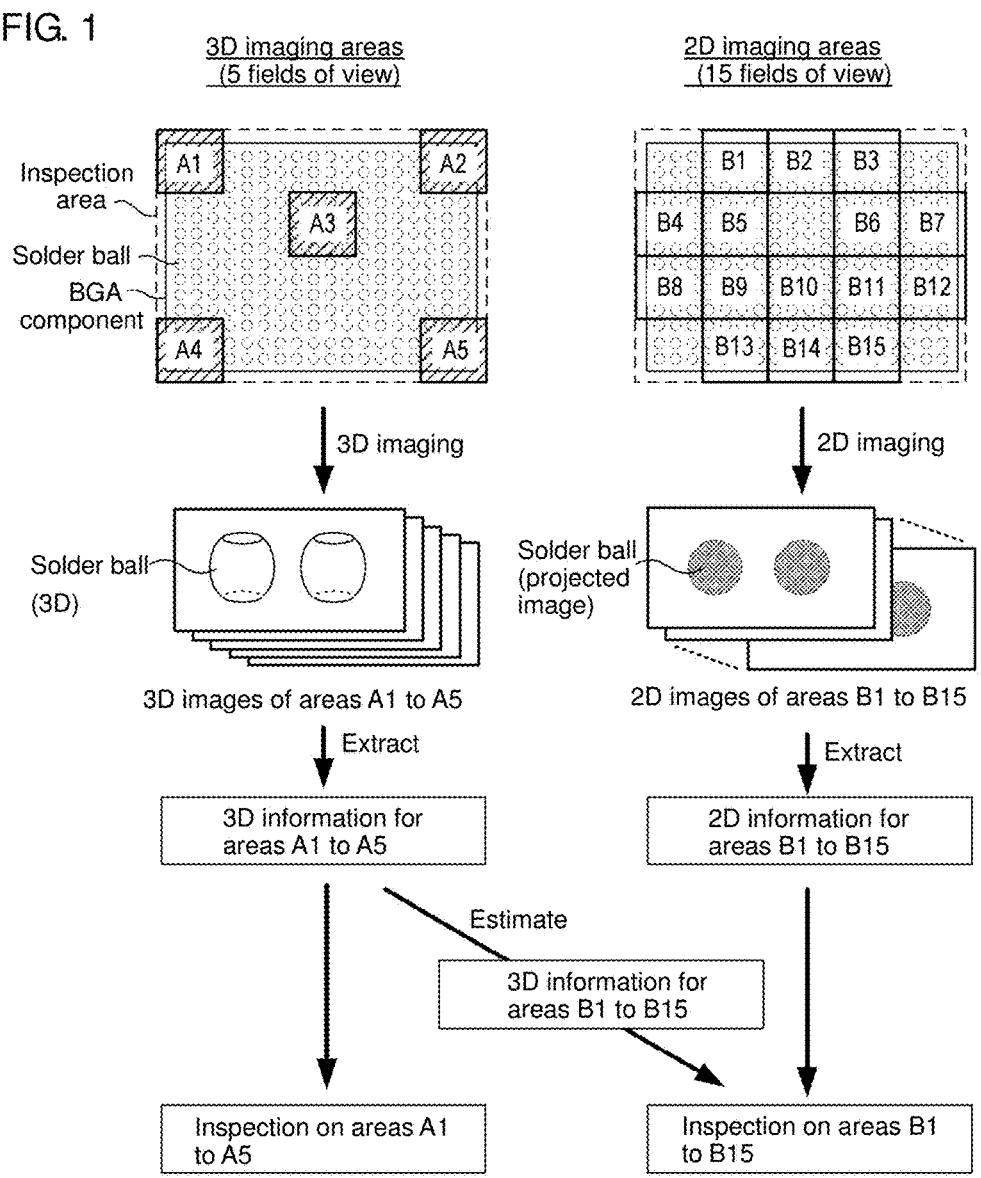
FIG. 1 is a schematic diagram illustrating 2D/3D-combined inspection.

FIG. 1 is a schematic diagram describing 2D/3D-combined inspection of a BGA component. In this example, an inspection area defined to contain the entire component (indicated with a broken line) is divided into 20 five-by-four matrix areas. Each area corresponds to a field of view of an imaging system. 3D images are captured for five areas A1 to A5 (hatched rectangles), which are the areas at the four corners and one area in the center. 2D images are captured for the remaining areas B1 to B15. The BGA component includes solder balls with substantially the same size and the same shape arranged in a predetermined regular pattern. Thus, 3D information for solder balls included in the areas A1 to A5 obtained by 3D imaging can be used to estimate 3D information for solder balls included in the remaining areas B1 to B15 through geometric calculations (e.g., interpolation and extrapolation). The 2D imaging areas B1 to B15 can thus undergo pseudo 3D inspection using the 3D information for the areas B1 to B15 that is estimated from the 3D information for the areas A1 to A5, in addition to 2D information obtained from the 2D images of the areas B1 to B15.

The 2D/3D-combined inspection is useful for inspecting an area larger than the field of view of the imaging system, or is useful when the inspection area is to be divided into two or more areas for imaging. The inspection area may be divided in any manner and into any other number of areas. The areas may be assigned to either 2D imaging or 3D imaging in any manner (hereafter referred to as the field of view assignment). As shown in FIG. 1, for example, the areas at the four corners and the central area may be assigned to 3D imaging, and the other areas may be assigned to 2D imaging automatically in accordance with predetermined rules. The field of view assignment may also be performed manually by an operator. In some embodiments, as shown in FIG. 2A, all the areas may be assigned to at least 2D imaging (the four corner areas undergo both 2D imaging and 3D imaging in this case). As shown in FIG. 2B, the field of view may be defined differently between 3D imaging and 2D imaging. Further, as shown in FIG. 2C, any area having a component on its back may be assigned to 3D imaging with higher priority than other areas, because an area with a component on its back cannot be captured by 2D imaging.

The 2D/3D-combined inspection is also useful for, for example, solder inspection for electronic components placed on a tray (tray inspection), in addition to the surface mounting board inspection.

X-Ray Inspection Apparatus

Figure 3:
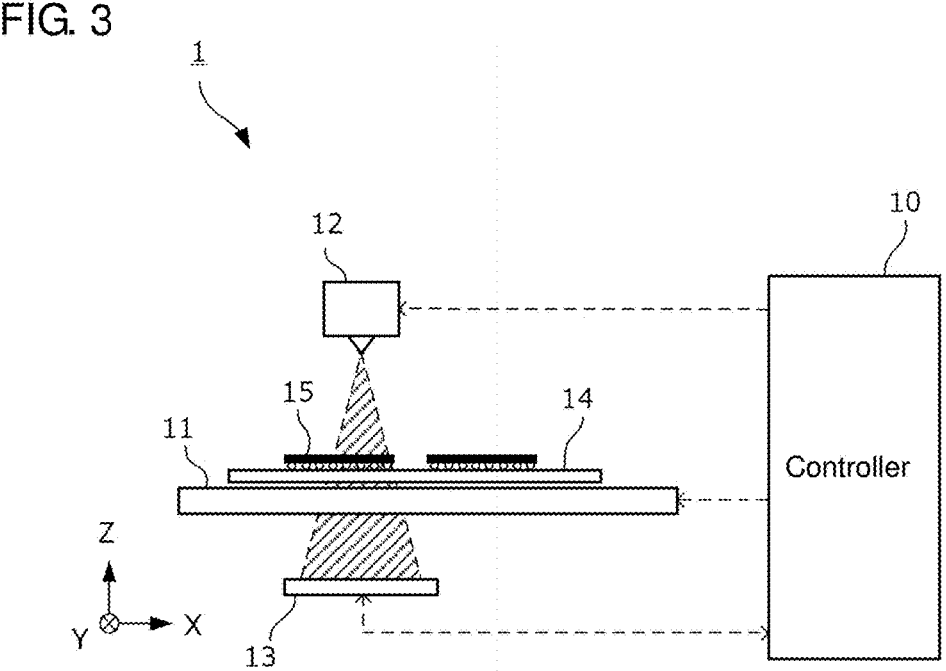
FIG. 3 is a diagram illustrating the hardware configuration of an X-ray inspection apparatus.

The specific structure of the X-ray inspection apparatus having the 2D/3D-combined inspection function will now be described in detail. FIG. 3 is a schematic diagram showing the hardware configuration of the X-ray inspection apparatus according to the embodiment.

An X-ray inspection apparatus 1 mainly includes a controller 10, a stage 11, an X-ray source 12, and an X-ray detector 13. The X-ray inspection apparatus 1 is used to inspect a solder joint on a component 15 mounted on a circuit board 14. As shown in FIG. 3, an XYZ-orthogonal coordinate system is defined to have the XY-plane parallel to the board surface and the Z-axis orthogonal to the board surface.

The X-ray source 12 irradiates the circuit board 14 with X-rays, and includes an X-ray generator that generates, for example, a cone beam or a fan beam. The X-ray detector 13 is an imaging unit that detects X-rays transmitted through the circuit board 14 and outputs data representing the obtained X-ray transmission image. The X-ray detector 13 may include a scintillator and a two-dimensional complementary metal oxide semiconductor (CMOS) sensor. The stage 11 is used to retain and transport the circuit board 14, and align the component 15 with the field of view of the imaging system including the X-ray source 12 and the X-ray detector 13. To move the field of view, either the stage 11 or the imaging system (the X-ray source 12 and the X-ray detector 13) may be moved, or both the stage 11 and the imaging system may be moved.

The X-ray inspection apparatus 1 can perform 2D imaging for capturing a 2D image through a single X-ray irradiation, and 3D imaging for capturing a 3D image through multiple X-ray irradiations. In 2D imaging, the circuit board is irradiated with X-rays applied in a direction orthogonal to the board surface (namely, Z-direction). In 3D imaging, multiple images are captured for a single field of view by changing the direction in which the X-rays are applied. The X-ray inspection apparatus 1 thus also includes a moving mechanism (not shown) for changing the irradiation direction of X-rays to the circuit board 14. The moving mechanism may operate in any of the modes in which, for example, the X-ray source 12 and the X-ray detector 13 rotate about the circuit board 14, the X-ray source 12 and the X-ray detector 13 are fixed and the circuit board 14 rotates on its axis, or the X-ray source 12 and the X-ray detector 13 each turn while having the circuit board 14 being sandwiched between the detectors.

The controller 10 controls the X-ray inspection apparatus 1 to perform processes (e.g., moving the field of view, irradiating X-rays, obtaining X-ray transmission images, generating 2D images, generating 3D images, estimating 3D geometric information, processing inspection, communicating with external devices and transferring data). The controller 10 may be a general-purpose computer including, for example, a central processing unit (CPU, or processor), a memory, a storage (e.g., hard disk drive), an input device (e.g., a keyboard, a mouse, or a touch panel), a display, and a communication interface (I/F). In this case, the controller 10 may be implemented using a single computer or may be implemented using multiple computers operating together. The controller 10 may be implemented using techniques including distributed computing and cloud computing. The functions of the controller 10, which will be described later, are implemented by the CPU (processor) executing the intended programs. All or some of the functions may be implemented using a circuit such as an application specific integrated circuit (ASIC) or a field programmable gate array (FPGA).

Controller

Figure 4:
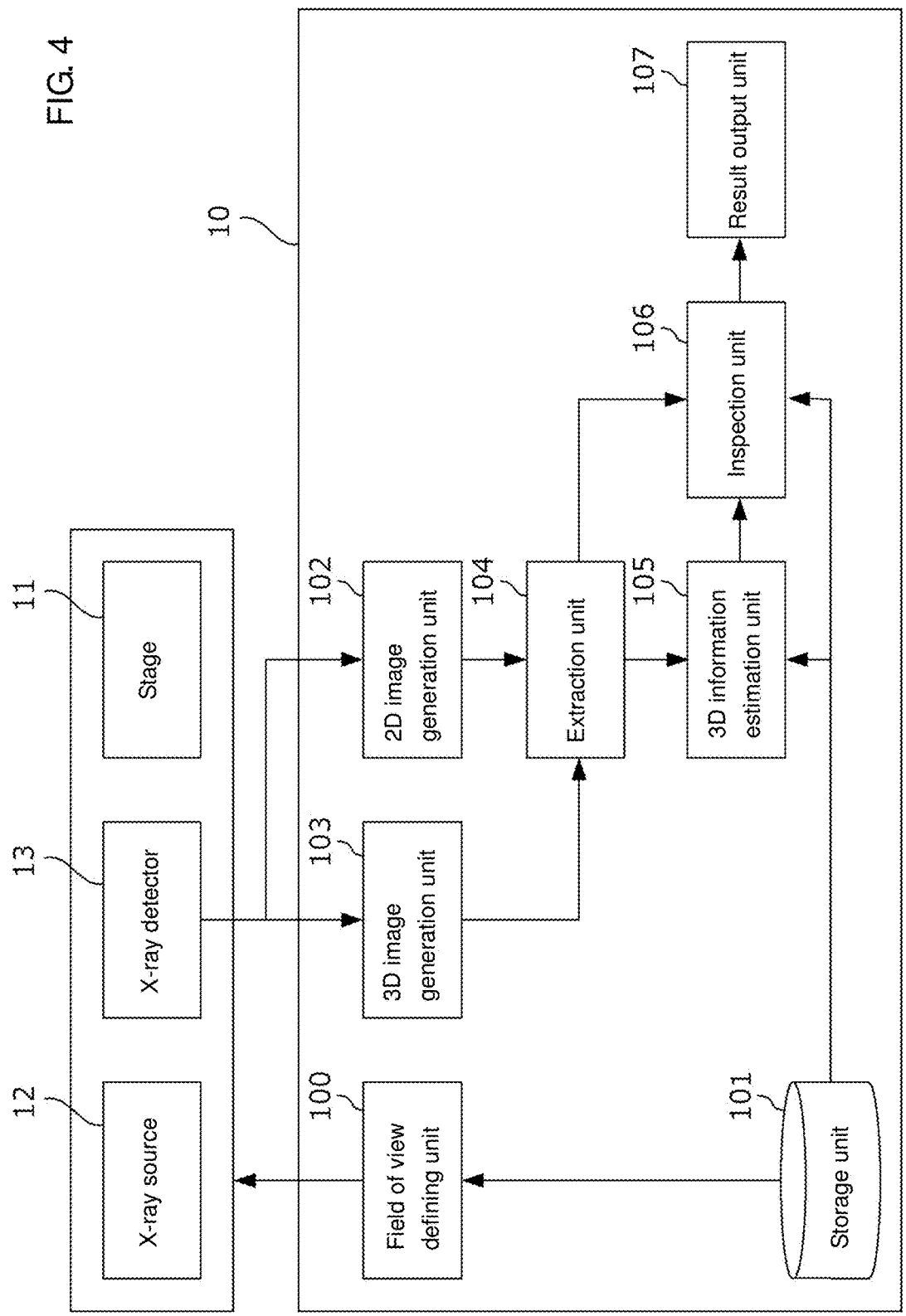
FIG. 4 is a functional block diagram of an X-ray inspection apparatus.

FIG. 4 is a functional block diagram of the controller 10. The controller 10 includes, as its functional units, a view field defining unit 100, a storage unit 101, a 2D image generation unit 102, a 3D image generation unit 103, an extraction unit 104, a 3D information estimation unit 105, an inspection unit 106, and a result output unit 107.

The view field defining unit 100 defines an inspection area, divides the inspection area into multiple areas, and assigns the field of view to each area in 2D/3D-combined inspection.

The storage unit 101 stores setting files and inspection programs for the X-ray inspection apparatus 1. The setting files include, for example, data describing the setting values for the X-ray source 12 and the X-ray detector 13. The inspection programs are data that define the procedure for the X-ray inspection, and are prepared and stored in advance for each type of inspection workpiece. The inspection programs may include information for the inspection workpiece and the inspection targets (e.g., board sizes, the item numbers, positions, and sizes of components), the conditions to be used in the field of view assignment for each component type, and the inspection logics (e.g., measurement items to be obtained from the image, the inspection criteria used in the inspection, such as a threshold or a range of values, and the processing in accordance with the determination results). The storage unit 101 is a nonvolatile storage medium.

The 2D image generation unit 102 generates a 2D image of the component 15 (e.g., a transmission image) using data obtained through a single X-ray irradiation. In the present embodiment, the X-ray source 12, the X-ray detector 13, and the 2D image generation unit 102 form a 2D processing unit that performs 2D imaging.

The 3D image generation unit 103 generates a 3D image of the component 15 (e.g., volume data) using data obtained through multiple X-ray irradiations. In the present embodiment, the X-ray source 12, the X-ray detector 13, and the 3D image generation unit 103 form a 3D processing unit that performs 3D imaging. Computed tomography (CT), tomosynthesis, or other 3D imaging techniques may be used. The 3D images may be reconstructed with any algorithm selected from, for example, simple back projection, filtered back projection, simultaneous reconstruction technique (SIRT), algebraic reconstruction technique (ART), or a search algorithm (e.g., a gradient method, a conjugate gradient method, and a steepest descent method).

The extraction unit 104 extracts (measures) information for an inspection target from its 2D image and its 3D image. 2D information extracted from the 2D image includes, for example, geometric information including the position, size, width, distance, surface area, and shape of the inspection target in the XY-plane. 3D information extracted from the 3D image includes, for example, geometric information including the position, size, height, distance, cross-sectional area at a given section, volume, and shape of the inspection target in the XYZ-space. Any information other than such geometric information may also be extracted. The 3D information estimation unit 105 estimates 3D information for inspection targets captured in the 2D image based on the information extracted from the 3D image and the information extracted from the 2D image. The inspection unit 106 inspects the inspection targets using the information extracted by the extraction unit 104 and the information estimated by the 3D information estimation unit 105. The result output unit 107 outputs the information extracted by the extraction unit 104, the information estimated by the 3D information estimation unit 105, and the inspection results obtained from the inspection unit 106 to a display or an external device. These functions will be described in detail later.

Operation of X-Ray Inspection Apparatus

Figure 5:
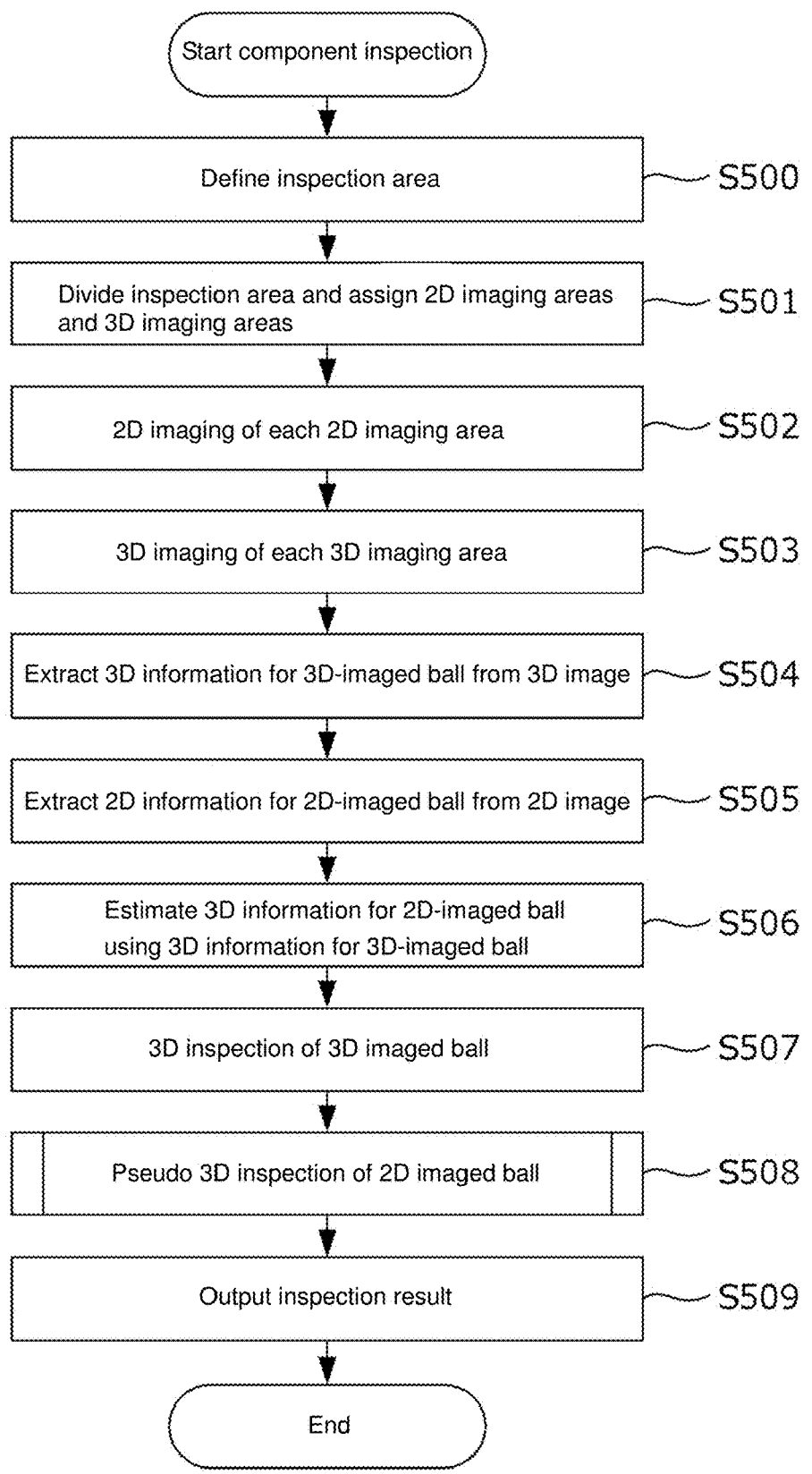
FIG. 5 is a flowchart illustrating a 2D/3D-combined inspection process.

Referring now to a flowchart in FIG. 5, a 2D/3D-combined inspection process performed by the X-ray inspection apparatus 1 will be described.

When the inspection is started, the view field defining unit 100 first reads information about a component to be inspected from the storage unit 101, and defines an inspection area for the component (step S500). The inspection area is usually defined to contain all inspection targets (solder balls) included in the component. The view field defining unit 100 then compares the size of the inspection area with the size of the field of view of the imaging system. When the inspection area is larger than the field of view (in other words, when the entire inspection area cannot be captured in a single shot), the view field defining unit 100 divides the inspection area into multiple areas, and performs the field of view assignment for 2D imaging and for 3D imaging (step S501). The view field defining unit 100 may divide the area and assign the field of view to each area in accordance with an instruction input from an operator, or may divide the area and perform the field of view assignment automatically in accordance with predetermined rules stored in the storage unit 101 (the conditions for the field of view assignment). In the example shown in FIG. 1, 3D imaging is assigned to areas A1 to A5, and 2D imaging is assigned to areas B1 to B15. For identification purpose, solder balls included in the 3D imaging areas A1 to A5 referred to as either 3D-imaged balls or first inspection targets, and solder balls included in the 2D imaging areas B1 to B15 are referred to as either 2D-imaged balls or second inspection targets.

Subsequently, each of the imaging areas B1 to B15 undergoes 2D imaging. The 2D image generation unit 102 thus generates 2D images (step S502). Similarly, each of the imaging areas A1 to A5 undergoes 3D imaging. The 3D image generation unit 103 thus generates 3D images (step S503).

Figure 6:
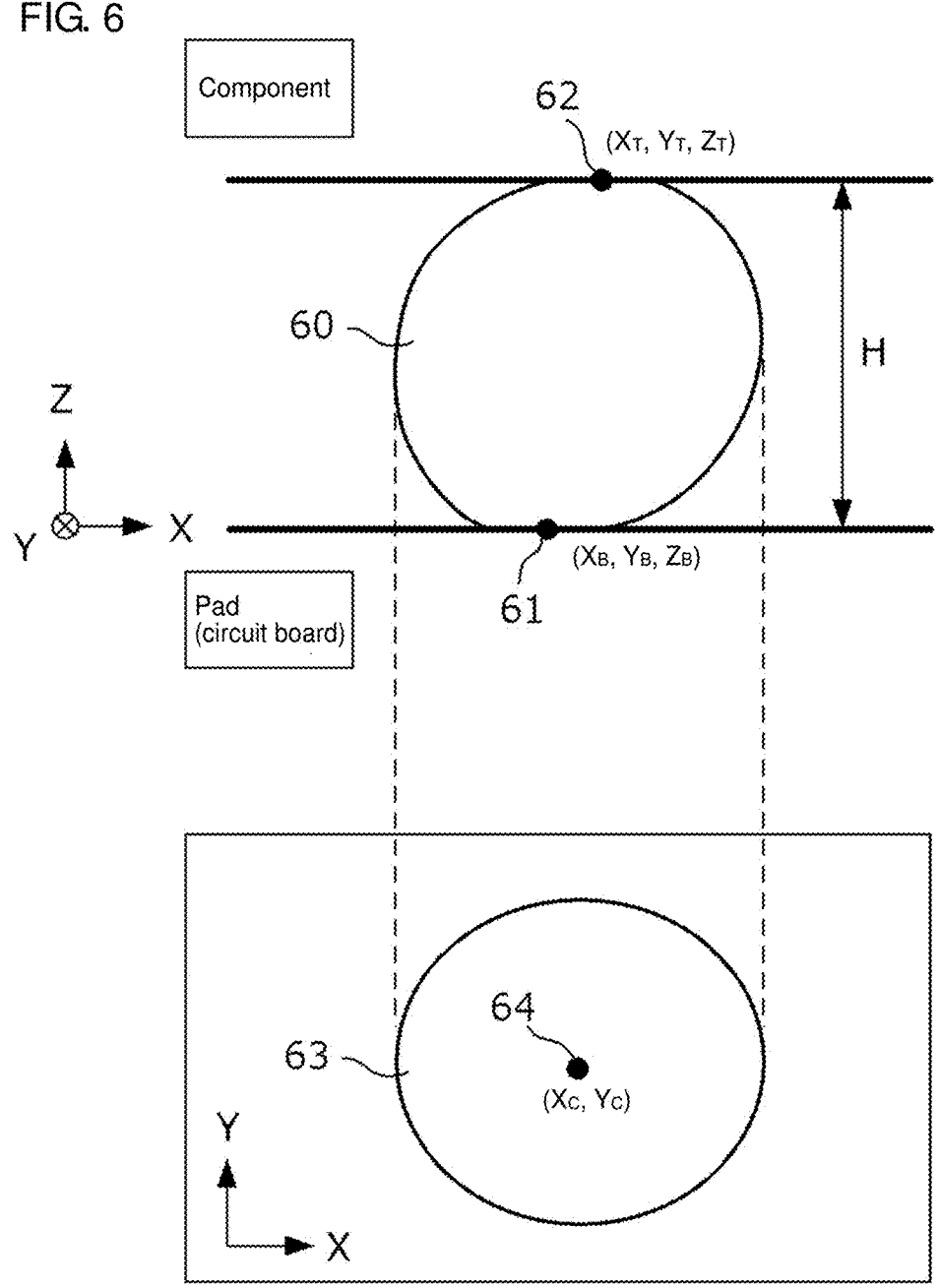
FIG. 6 is a diagram illustrating an example of 3D information for a 3D-imaged ball extracted from a 3D image.

The extraction unit 104 then analyzes the 3D images obtained from the 3D imaging areas (first areas) A1 to A5, and extracts 3D information for the 3D-imaged balls included in each area (step S504). As shown in FIG. 6, the extraction unit 104 extracts, as 3D information, the position $(X_B, Y_B, Z_B)$ of a pad end (first end) 61 of a solder ball 60, the position $(X_T, Y_T, Z_T)$ of a component end (second end) 62 of the solder ball 60, the height H $(=Z_T-Z_B)$ of the solder ball 60 in Z-direction, a surface area A of a projected image 63 of the solder ball 60 in the XY-plane, the position $(X_C, Y_C)$ of a center 64 of the projected image 63 of the solder ball 60 in the XY-plane, and volumetric information V for the solder ball 60 in the present embodiment.

Although the volumetric information V may be calculated as a precise volume value based on the 3D shape of the solder ball 60, the volume value in the present embodiment is approximated using the formula below in a simplified manner. This resultant approximate value V enables sufficiently accurate quality determination in a nonwetting inspection process (described later).

Figure 7:
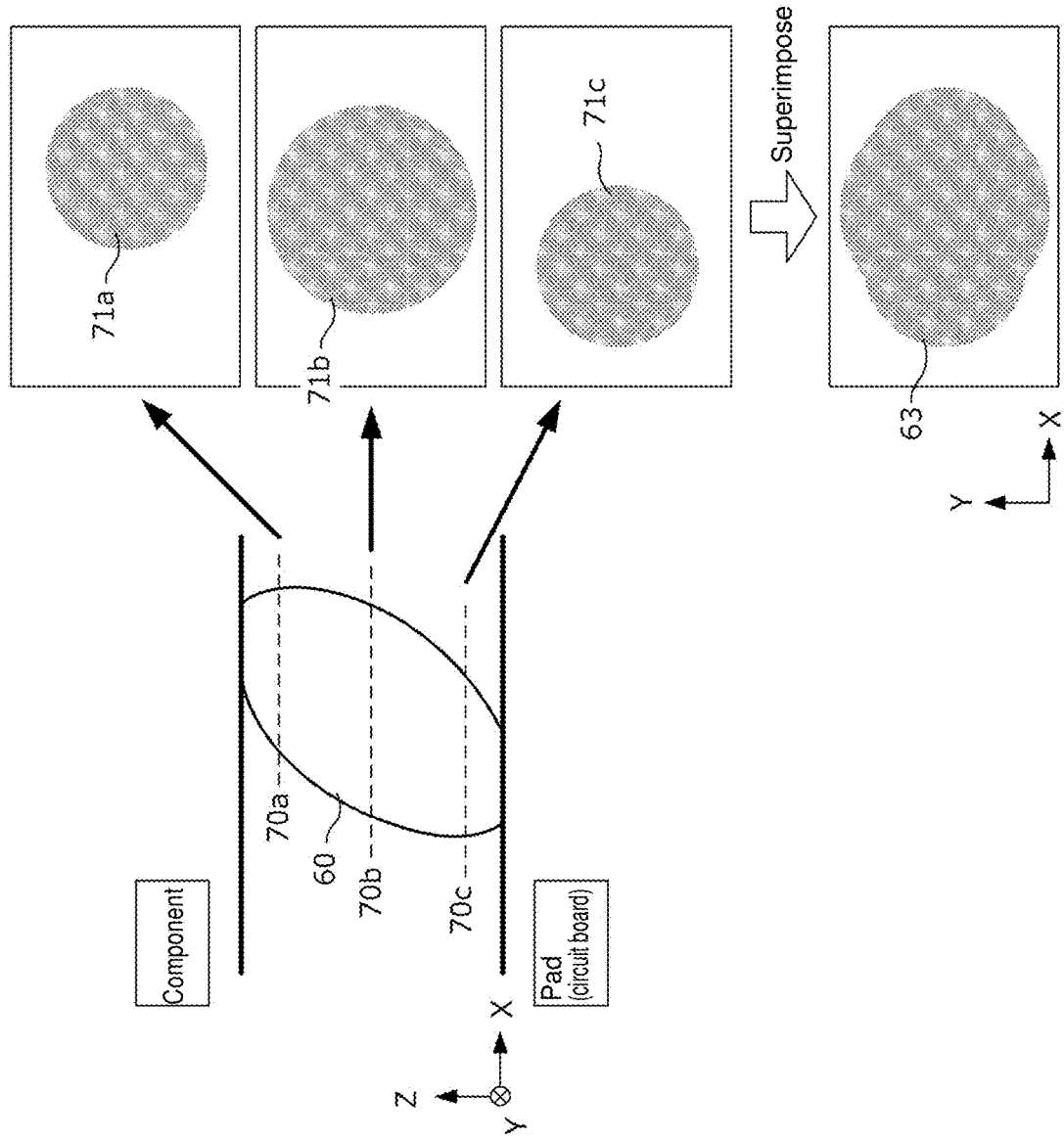
FIG. 7 is a diagram illustrating generation of a projected image of a solder ball using a 3D image.

Volumetric information $V$=solder ball height $H$ in Z-direction×projected solder ball image surface area $A$ The projected image 63 of the solder ball 60 may be obtained with any method. As shown in FIG. 7, for example, a plurality of XY sliced images 71a, 71b, and 71c respectively corresponding to positions 70a, 70b, and 70c, which differ from one another in Z-direction, are obtained from a 3D image of the solder ball 60. These sliced images may be superimposed on one another to estimate the shape of the projected image 63 in a simplified manner. In some embodiments, the solder ball 60 included in the 3D imaging area may also use 2D imaging to actually obtain the projected image of the solder ball 60.

Figure 8:
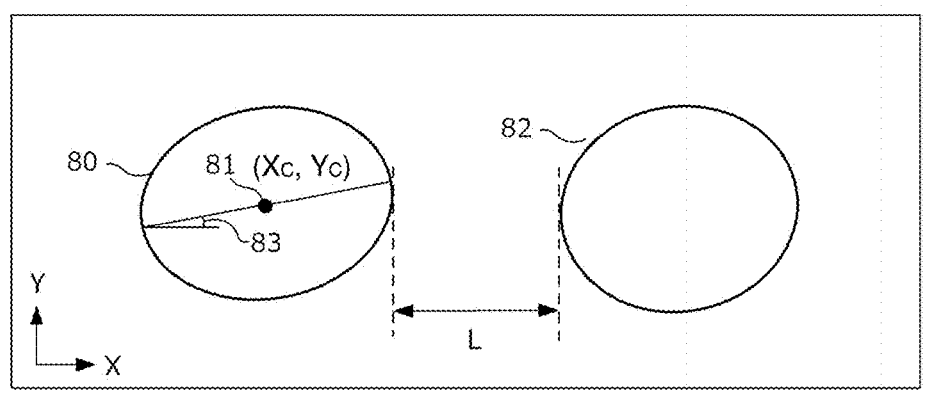
FIG. 8 is a diagram illustrating 2D information for a 2D-imaged ball extracted from a 2D image.

The extraction unit 104 then analyzes the 2D images obtained from the 2D imaging areas (second areas) B1 to B15, and extracts 2D information for the 2D-imaged ball included in each area (step S505). As shown in FIG. 8, for example, the extraction unit 104 extracts, as 2D information, the position $(X_C, Y_C)$ of a center 81 of a solder ball 80 in the XY-plane, a surface area A of the solder ball 80, an inter-solder distance L between the solder ball 80 and an adjacent solder ball 82 (adjacent inspection target), and the circularity or a major diameter angle 83 of the solder ball. The circularity of a solder ball indicates the degree of closeness of the outer shape of its projected image to the outer shape a geometrically perfect circle. The circularity is 100% when the outer shape is identical to the outer shape of a perfect circle, and is represented by a smaller value as the degree of closeness to the perfect circle is lower. The circularity can be calculated with a formula using, as its variables, a major or minor diameter, a surface area, a circumference, or other features of the outer shape. The major diameter angle 83 is an angle between the major diameter of the projected solder ball image and the X-axis.

The 3D information estimation unit 105 then estimates 3D information for each of the 2D-imaged balls (step S506) included in the 2D imaging areas B1 to B15 using the 3D information for the 3D-imaged ball obtained in step S504. In the present embodiment, four values are calculated: (1) 2D-imaged ball height in Z-direction, (2) 2D-imaged ball volumetric information, (3) 2D-imaged ball theoretical position, and (4) 2D-imaged ball deviation between the pad end and the component end. These values may be calculated with methods exemplified below.

1. 2D-Imaged Ball Height in Z-Direction

FIGS. 9A to 9C are diagrams describing one method for approximate calculation of the height of a 2D-imaged ball in Z-direction using 3D information obtained for a 3D-imaged ball. FIGS. 9A to 9C are side views of 3D-imaged balls SB1 and SB4 indicated with solid lines and 2D-imaged balls SB2, SB3, and SB5 indicated with broken lines. For ease of explanation, the 3D- and the 2D-imaged balls are arranged in one-dimension in this example. The same approximate calculation can be used for 3D- and the 2D-imaged balls arranged in two-dimensions as shown in FIG. 1.

The 3D information estimation unit 105 uses, as 3D information for the 3D-imaged ball, the coordinates indicating the 3D position of each of the pad end and the component end (indicated by black dots in FIG. 9A). In FIG. 9A, $(X1_B, Y1_B, Z1_B)$ is the XYZ-position of the pad end of the 3D-imaged ball SB1, and $(X1_T, Y1_T, Z1_T)$ is the XYZ-position of the component end of the 3D-imaged ball SB1. Also, $(X4_B, Y4_B, Z4_B)$ is the XYZ-position of the pad end of the 3D-imaged ball SB4, and $(X4_T, Y4_T, Z4_T)$ is the XYZ-position of the component end of the 3D-imaged ball SB4.

The 3D information estimation unit 105 uses, as 2D information for the 2D-imaged ball, the coordinates indicating the 2D position of the center of the solder ball (indicated by dot-and-dash lines in FIG. 9B). In FIG. 9B, $(X2_C, Y2_C)$, $(X3_C, Y3_C)$, and $(X5_C, Y5_C)$ are the XY-positions of the centers of the 2D-imaged balls SB2, SB3, and SB5, respectively.

The 3D information estimation unit 105 interpolates or extrapolates the 3D-position coordinates of the pad ends of the 3D-imaged balls SB1 and SB4 to calculate the Z-positions $Z2_B$, $Z3_B$, and $Z5_B$ for the pad ends of the 2D-imaged balls SB2, SB3, and SB5 at their XY-positions. The 3D information estimation unit 105 also interpolates or extrapolates the 3D-position coordinates of the component ends of the 3D-imaged balls SB1 and SB4 to calculate the Z-positions $Z2_T$, $Z3_T$, and $Z5_T$ for the component ends of the 2D-imaged balls SB2, SB3, and SB5 at their XY-positions. The hollow dots in FIG. 9C indicate the positions of the pad ends and the component ends of the 2D-imaged balls, which are calculated through interpolation or extrapolation. The interpolation or extrapolation method may use approximation using linear equations (linear interpolation or linear extrapolation), or may use approximation using n-degree polynomials (n≥2).

The 3D information estimation unit 105 then calculates the height H of each 2D-imaged ball in Z-direction ($H=Z_T-Z_B$) based on the Z-position of the corresponding pad end and the Z-position of the corresponding component end obtained through approximation. The approximate calculation described above allows sufficiently accurate estimation of the height of the 2D-imaged ball in Z-direction, because the Z-positions of the pad end and the component end of each solder ball are assumed to deviate constantly along a warp or a slant in the circuit board or in the component.

In the present embodiment, the Z-position of the pad end and the Z-position of the component end are calculated separately, and then the difference between the obtained Z-positions are calculated to determine the solder ball height in Z-direction. The approximate calculation method to obtain the Z-direction height may not be limited to the above examples. For example, the height of a plurality of 3D-imaged balls in Z-direction may be calculated first, and then the obtained height may be interpolated or extrapolated to directly determine the height of each 2D-imaged ball in Z-direction corresponding to its XY-position.

2. 2D-Imaged Ball Volumetric Information

Figure 10:
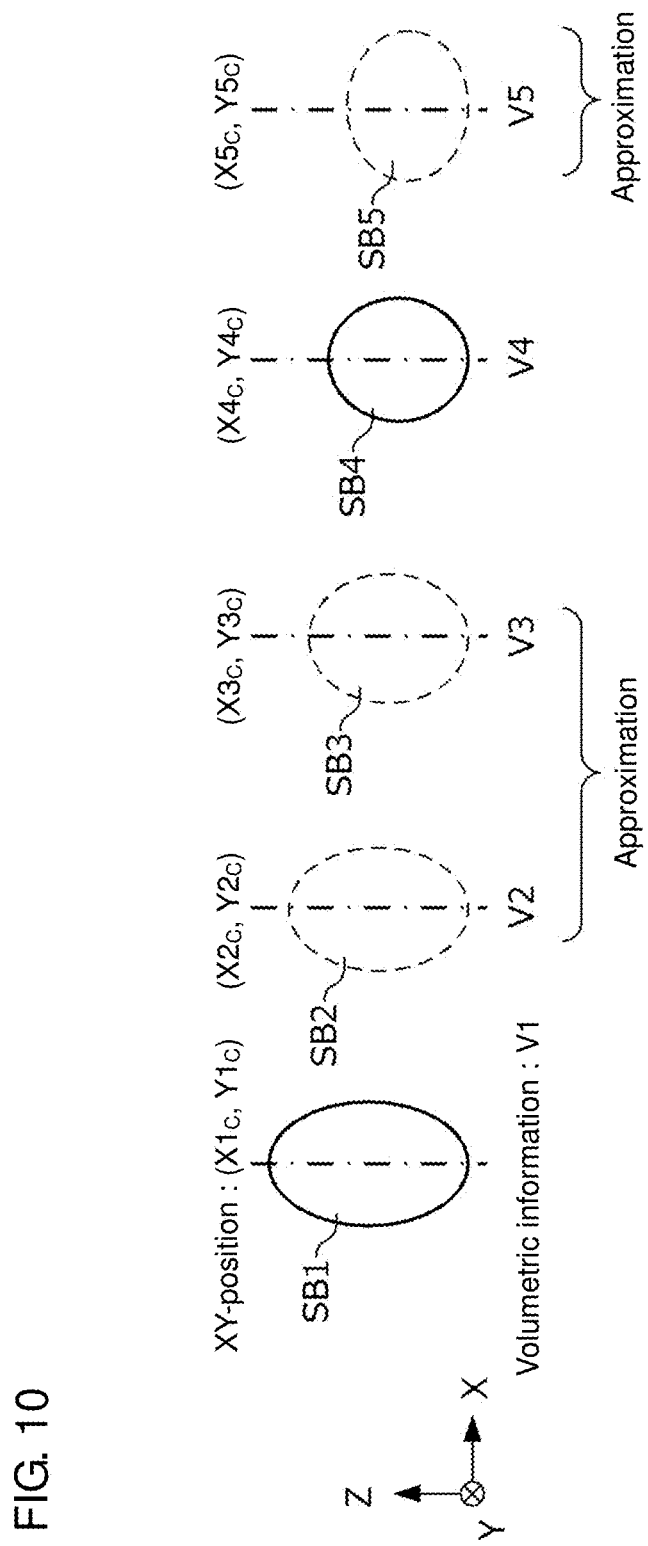
FIG. 10 is a diagram illustrating a method for approximate calculation of volumetric information for a 2D-imaged ball.

FIG. 10 is a diagram describing one method for approximate calculation of volumetric information for a 2D-imaged ball using 3D information obtained for a 3D-imaged ball. FIG. 10 is a side view of 3D-imaged balls SB1 and SB4 indicated with solid lines and 2D-imaged balls SB2, SB3, and SB5 indicated with broken lines. For ease of explanation, the 3D- and 2D-imaged balls are arranged in one-dimension in this example. The same approximate calculation can be used for 3D- and 2D-imaged balls arranged in two-dimensions as shown in FIG. 1.

The 3D information estimation unit 105 uses, as 3D information for the 3D-imaged ball, the coordinates indicating the 2D position of the center of the solder ball and its volumetric information. In FIG. 10, $(X1_C, Y1_C)$ is the XY-position of the center of the 3D-imaged ball SB1, and V1 is its volumetric information. Also, $(X4_C, Y4_C)$ is the XY-position of the center of the 3D-imaged ball SB4, and V4 is its volumetric information. The 3D information estimation unit 105 further uses, as 2D information for the 2D-imaged ball, the coordinates indicating the 2D position of the center of the solder ball. In FIG. 10, $(X2_C, Y2_C)$, $(X3_C, Y3_C)$, and $(X5_C, Y5_C)$ are respectively the XY-positions of the centers of the 2D-imaged balls SB2, SB3, and SB5.

The 3D information estimation unit 105 interpolates or extrapolates the volumetric information sets V1 and V4 for the 3D-imaged balls SB1 and SB4 to calculate volumetric information sets V2, V3, and V5 for the 2D-imaged balls SB2, SB3, and SB5 at their XY-positions. The interpolation or extrapolation method may use approximation using linear equations (linear interpolation or linear extrapolation), or may use approximation using n-degree polynomials (n≥2).

3. 2D-Imaged Ball Theoretical Position

Figure 11A:
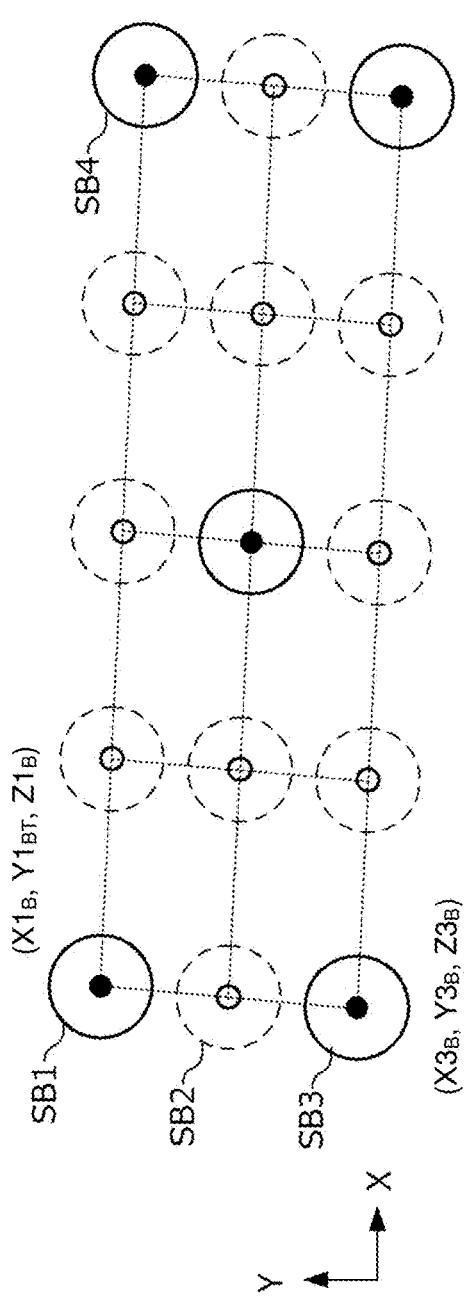
FIGS. 11A and 11B are diagrams illustrating a method for approximate calculation of a theoretical position of a 2D-imaged ball.
Figure 11B:
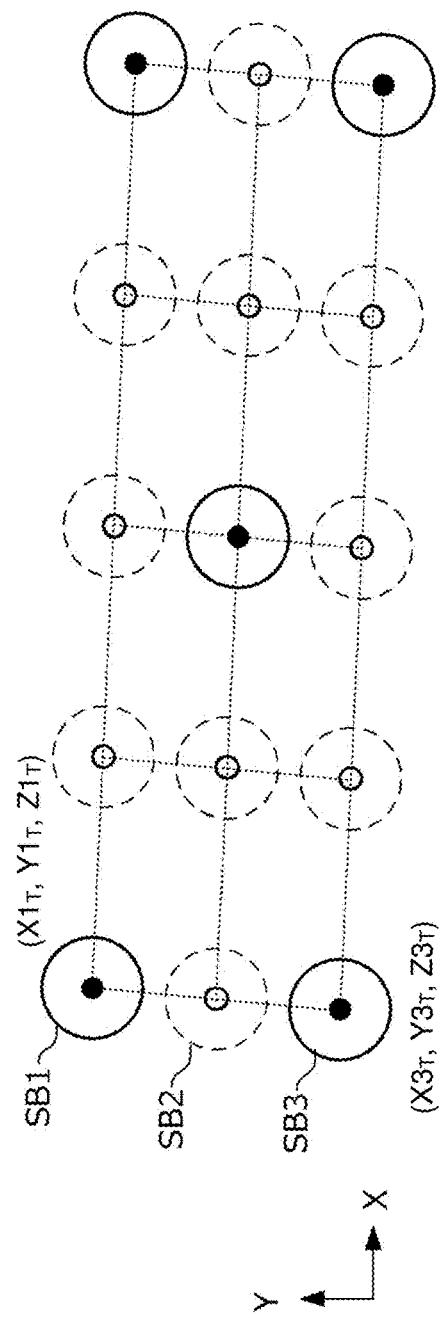

FIGS. 11A and 11B are diagrams describing one method for approximate calculation of a predicted XY-position (theoretical position) of a 2D-imaged ball using 3D information for a 3D-imaged ball. FIG. 11A is a top view of a pad end at an XY-position. FIG. 11B is a top view of a component end at an XY-position. In the figure, solid lines indicate 3D-imaged balls, and broken lines indicate 2D-imaged balls.

The 3D information estimation unit 105 uses, as 3D information for the 3D-imaged ball, the coordinates indicating the 3D position of the pad end (indicated by black dots in FIG. 11A) and the coordinates indicating the 3D position of the component end (indicated by black dots in FIG. 11B). In the examples shown in FIGS. 11A and 11B, $(X1_B, Y1_B, Z1_B)$ is the XYZ-position of the pad end of the 3D-imaged ball SB1, and $(X1_T, Y1_T, Z1_T)$ is the XYZ-position of the component end of the 3D-imaged ball SB1. Also, $(X3_B, Y3_B, Z3_B)$ is the XYZ-position of the pad end of the 3D-imaged ball SB3, and $(X3_T, Y3_T, Z3_T)$ is the XYZ-position of the component end of the 3D-imaged ball SB3.

The 3D information estimation unit 105 refers to inspection programs stored in the storage unit 101, and obtains positional information for solder balls included in the inspection target component. The positional information indicates, for example, the number of solder balls, their arrangement, and the distance between the solder balls, which define the designed positions of the solder balls. In the example shown in FIG. 11A, the positional information represents fifteen solder balls arranged in a three-by-five matrix at equal intervals.

The 3D information estimation unit 105 then calculates the positional relationship of 2D-imaged balls relative to 3D-imaged balls using the positional information for the solder balls. In the example shown in FIG. 11A, the positional information indicates that the 2D-imaged ball SB2 is at the midpoint between the 3D-imaged balls SB1 and SB3, and three 2D-imaged balls are arranged at equal intervals between the 3D-imaged balls SB1 and SB4. The 3D information estimation unit 105 then interpolates or extrapolates the 3D-position coordinates of the pad end and the component end of the 3D-imaged balls based on the positional relationship between the 3D-imaged balls and the 2D-imaged balls that are calculated using the positional information, and calculates the 3D-position coordinates of the pad end and the component end of each 2D-imaged ball. The interpolation or extrapolation method may use approximation using linear equations (linear interpolation or linear extrapolation), or may use approximation using n-degree polynomials (n≥2).

In FIGS. 11A and 11B, the hollow dots indicate the pad ends of the 2D-imaged balls and the component ends of the 2D-imaged balls, which are calculated through interpolation or extrapolation. Using linear equations for approximation, for example, the 3D-position coordinates of the pad end of the 2D-imaged ball SB2 are calculated to be $((X1_B+X3_B)/2, (Y1_B+Y3_B)/2, (Z1_B+Z3_B)/2)$, and the 3D-position coordinates of the component end of the 2D-imaged ball SB2 are calculated to be $((X1_T+X3_T)/2, (Y1_T+Y3_T)/2, (Z1_T+Z3_T)/2)$. The XY-positions of the pad end and the component end are averaged to calculate the XY-position of the 2D-imaged ball SB2 to be $((X1_B+X3_B+X1_T+X3_T)/4, (Y1_B+Y3_B+Y1_T+Y3_T)/4)$.

The calculated position of the 2D-imaged ball is not the actual position of the 2D-imaged ball, but is a virtual position of the 2D-imaged ball estimated from the positional relationship of this 2D-imaged ball relative to the corresponding 3D-imaged balls, or in other words, a theoretical position at which the 2D-imaged ball is predicted to be placed. The calculated theoretical position of the 2D-imaged ball is used as a reference (correct) position of the 2D-imaged ball in the subsequent pseudo 3D inspection.

4. Pad End and Component End Deviation of 2D-Imaged Ball

The 3D information estimation unit 105 uses the XYZ-position of the pad end (first end) and the XYZ-position of the component end (second end) of the 2D-imaged ball, which are obtained through the process (3) to calculate a deviation between the pad end and the component end in the XY-plane (hereafter simply, a component-pad deviation). The component-pad deviation is an index indicating the degree of deviation of the component mounting position from the pad (or the circuit board). The component-pad deviation may also indicate a tilt of the solder ball, which is a tilt of the center axis of the solder ball (a straight line connecting the pad end to the component end) relative to the Z-axis.

After extracting the 3D information for the 3D-imaged balls (step S504), extracting the 2D information for the 2D-imaged balls (step S505), and estimating 3D information for the 2D-imaged balls (step S506) as described above, the processing then advances to inspection of each solder ball.

In step S507, the inspection unit 106 first performs 3D inspection of each 3D-imaged ball. The 3D inspection includes positional deviation inspection, mounting deviation inspection, nonwetting inspection, bridge inspection, and ball height inspection. The positional deviation inspection checks whether each solder piece does not deviate from its reference position. The inspection unit 106 compares, for example, the XY-position of the center of each solder ball with its reference position stored in the inspection programs. The inspection unit 106 determines that the inspection target is defective when the difference between the positions exceeds the threshold, and determines that the inspection target is acceptable when the difference does not exceed the threshold. The mounting deviation inspection checks whether the entire component does not deviate from the pads. The inspection unit 106 calculates, for example, component-pad deviations for all the solder balls included in the component, and determines that the component is defective when the maximum deviation exceeds the threshold, and determines that the component is acceptable when the maximum deviation does not exceed the threshold. The nonwetting inspection checks whether the solder on the component and the solder on the pad are properly joined together, without being apart from each other or being unfused. The bridge inspection checks whether adjacent electrodes are electrically connected (bridged) via the solder. The ball height inspection checks whether the solder ball height in Z-direction is too high or too low. For example, the inspection unit 106 determines that the component is defective when the solder ball height in Z-direction either exceeds a first threshold or is less than a second threshold (second threshold<first threshold), or otherwise determines that the component is acceptable. The inspection methods described above are mere examples, and any other 3D inspection methods including techniques known in the art may be used.

In step S508, the inspection unit 106 then performs pseudo 3D inspection of the 2D-imaged balls using the 3D information estimated in step S506. The pseudo 3D inspection includes positional deviation inspection, mounting deviation inspection, nonwetting inspection, bridge inspection, and ball height inspection. The specific procedure for the pseudo 3D inspection will be described later.

In step S509, the result output unit 107 outputs the results from the 3D inspection in step S507 and the results from the pseudo 3D inspection in step S508 to a display or to an external device. The result output unit 107 may output, for example, information about measurement values, sectional positions, XY-coordinates, and images used in each of the above inspection items, in addition to the determination results (either defective or acceptable) for each inspection item.

Pseudo 3D Inspection

The pseudo 3D inspection of the 2D-imaged ball performed in S508 in FIG. 5 will now be described in one example. The thresholds used in the inspection are predetermined appropriate values for each inspection item and for each type of component.

1. Positional Deviation Inspection of 2D-Imaged Ball

FIG. 12 is a flowchart showing a positional deviation inspection process performed for a 2D-imaged ball. The inspection unit 106 obtains the theoretical position (XY-position) of the 2D-imaged ball estimated from 3D information obtained for the corresponding 3D-imaged ball (step S120), and obtains the actual center position (XY-position) of the 2D-imaged ball measured from the 2D image (step S121). The inspection unit 106 then calculates the difference between the theoretical position and the actual position. When the difference does not exceed the threshold (Yes in step S122), the inspection unit 106 determines that the component is acceptable (step S123). When the difference exceeds the threshold (No in step S122), the inspection unit 106 determines that the component is defective due to its positional deviation (step S124).

2. Mounting Deviation Inspection of 2D-Imaged Ball

The inspection unit 106 obtains the component-pad deviation for the 2D-imaged ball estimated from the 3D information obtained for the 3D-imaged ball. The inspection unit 106 then determines that the component is defective when the deviation does not exceed the threshold, and determines that the component is acceptable when the deviation exceeds the threshold.

3. Wetting Inspection of 2D-Imaged Ball

FIG. 13 is a flowchart showing a nonwetting inspection process performed for a 2D-imaged ball. The inspection unit 106 first obtains the circularity (actual measurement value) of the 2D-imaged ball calculated from the 2D image (step S130). The inspection unit 106 then compares the circularity (actual measurement value) with its threshold (step S131).

When the circularity of the 2D-imaged ball is less than the threshold (No in step S131), the processing advances to an inspection to check whether the solder ball on the component and the solder paste piece on the pad are fused together or unfused (head in pillow). When the solder ball and the solder paste piece are fused together, the circularity of the solder ball may be assumed to depend on the component-pad deviation. The inspection unit 106 then estimates the circularity of the acceptable 2D-imaged ball using the component-pad deviation of the 2D-imaged ball (step S132). The inspection unit 106 then compares the estimated value with the actual circularity measurement value (step S133). When the difference between the estimated value and the actual measurement value does not exceed the threshold (Yes in step S133), the inspection unit 106 determines that the component is acceptable (step S134), and when the difference exceeds the threshold (No in step S133), the inspection unit 106 determines that the component is defective (unfused state) (step S135).

When the circularity of the 2D-imaged ball is not less than the threshold (Yes in step S131), the processing advances to an inspection to check whether the solder ball on the component and the solder paste piece on the pad have a gap between them. When the solder ball is spaced apart from the solder paste piece, the solder ball can have a larger projected surface area than expected for a solder ball in an acceptable state. The inspection unit 106 calculates volumetric information Va (actual measurement value) by multiplying the surface area A of the 2D-imaged ball calculated from the 2D image by the height of the 2D-imaged ball H in Z-direction estimated from the 3D information (step S136), obtains volumetric information Vb (estimated value) for the 2D-imaged ball estimated from the 3D information (step S137), and compares the actual measurement value Va of the volumetric information with the estimated value Vb (step S138). When the difference between the actual measurement value Va and the estimated value Vb does not exceed its threshold (Yes in step S138), the inspection unit 106 determines that the component is acceptable (step S139), and when the difference exceeds the threshold (No in step S138), the inspection unit 106 determines that the component is defective (open state) (step S140).

Although the circularity of the solder ball is used to evaluate the unfused state in the present embodiment, a major diameter angle may be used either in place of or in addition to the circularity. This is because the major diameter angle of a solder ball seemingly depends on the direction of the component-pad deviation.

4. Bridge Inspection of 2D-Imaged Ball

Figure 14A:
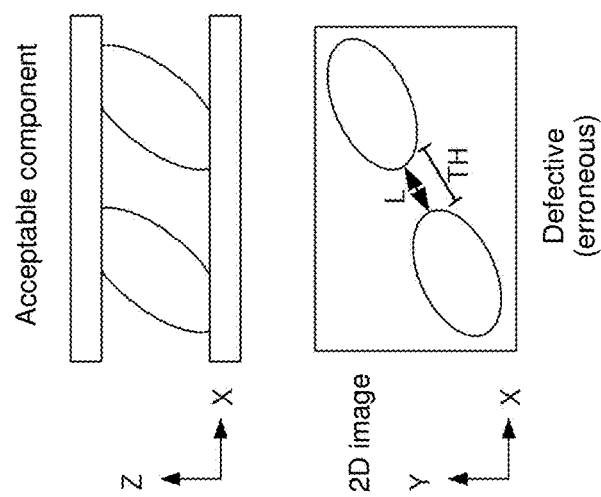
FIGS. 14A to 14C are diagrams illustrating bridge inspection in which the determination is difficult.
Figure 14B:
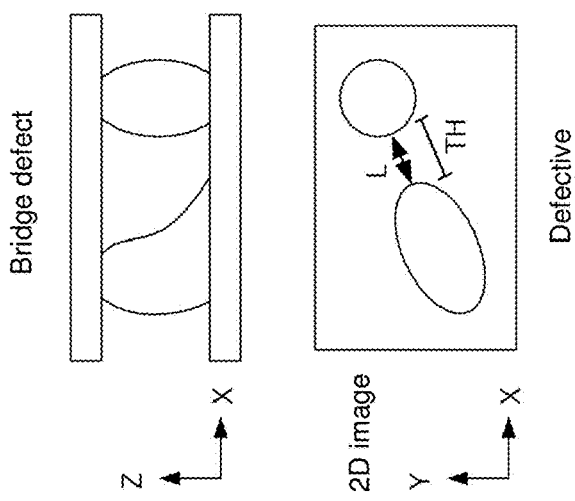
Figure 14C:
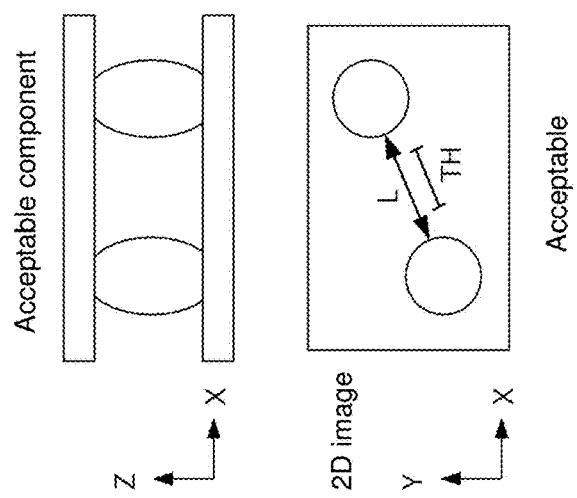

The bridge inspection detects not only a defective component including a bridge defect, but can also detect a component that is likely to have a bridge defect and is likely to be defective (a component with a small inter-solder distance between adjacent solder balls). However, determining whether a component is defective may be difficult simply by evaluating the inter-solder distance L measured from a 2D image. This will be described with reference to FIGS. 14A to 14C. FIG. 14A shows an example of an acceptable component. FIG. 14B shows an example of a component with a bridge defect. In these 2D images, the inter-solder distance L in FIG. 14A is sufficiently large, whereas the inter-solder distance L in FIG. 14B is apparently smaller. Thus, the component in FIG. 14A is determined acceptable and the component in FIG. 14B is determined defective properly by determining whether the inter-solder distance L exceeds the threshold TH. FIG. 14C shows another example of an acceptable component. In this example, the component deviates from the pad in the XY-plane with the solder balls tilting relative to the Z-axis. When the solder balls tilt more relative to the Z-axis, the projected image of the solder balls becomes larger, because the solder balls are projected in the XY-plane as a 2D image. The inter-solder distance (appearance distance) will thus be smaller in the 2D image. In this case, the acceptable component in FIG. 14C cannot be distinguished from the defective component in FIG. 14B by simply comparing the inter-solder distance L with the threshold TH. The acceptable component in FIG. 14C can be erroneously determined as defective.

The bridge inspection according to the present embodiment uses the component-pad deviation, in addition to the inter-solder distance L. More specifically, the threshold TH is dynamically changed in accordance with the component-pad deviation to reduce erroneous determination as in the example shown in FIG. 14C.

Figure 15:
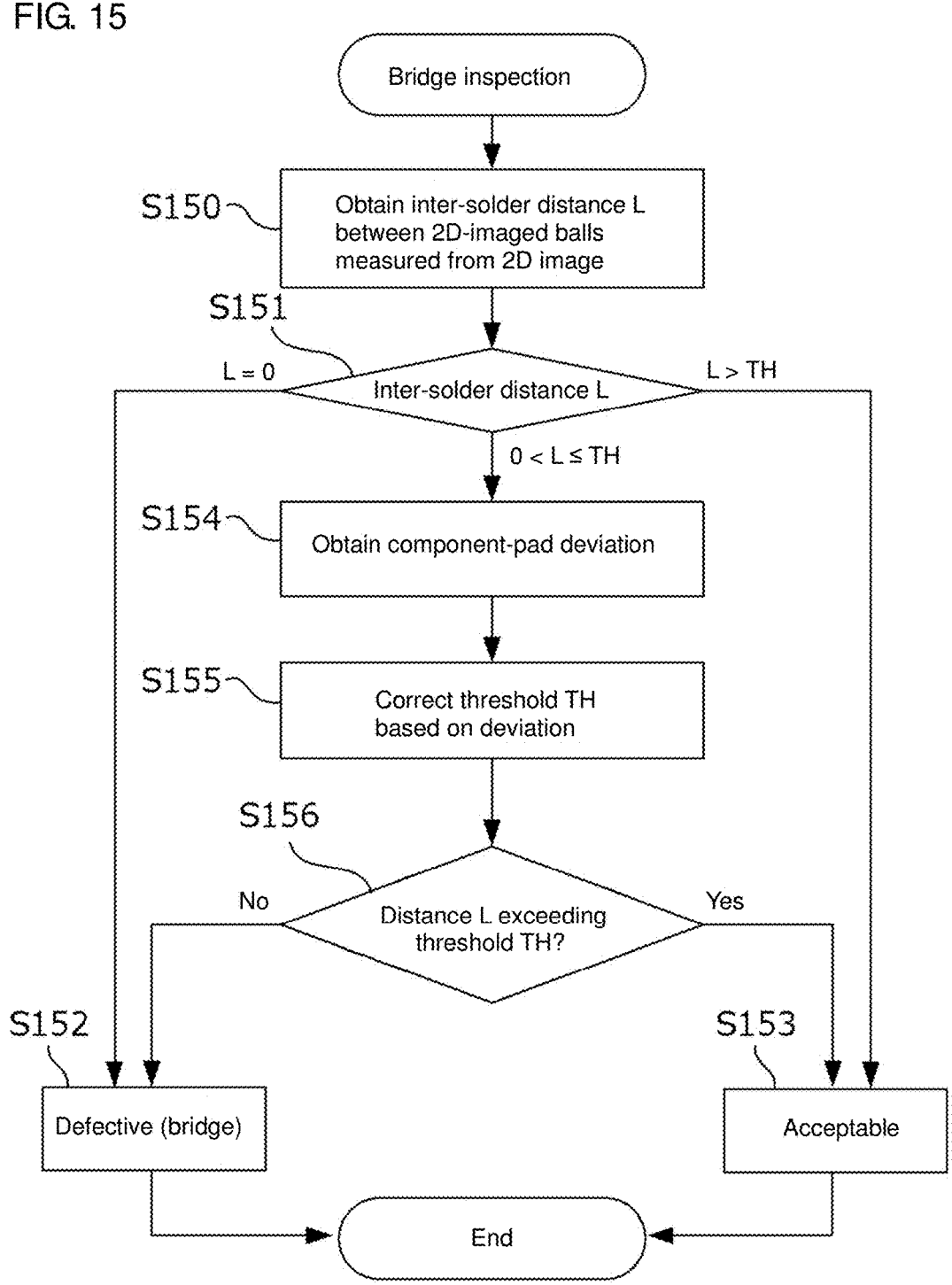
FIG. 15 is a flowchart illustrating a bridge inspection process for a 2D-imaged ball.
Figure 16A:
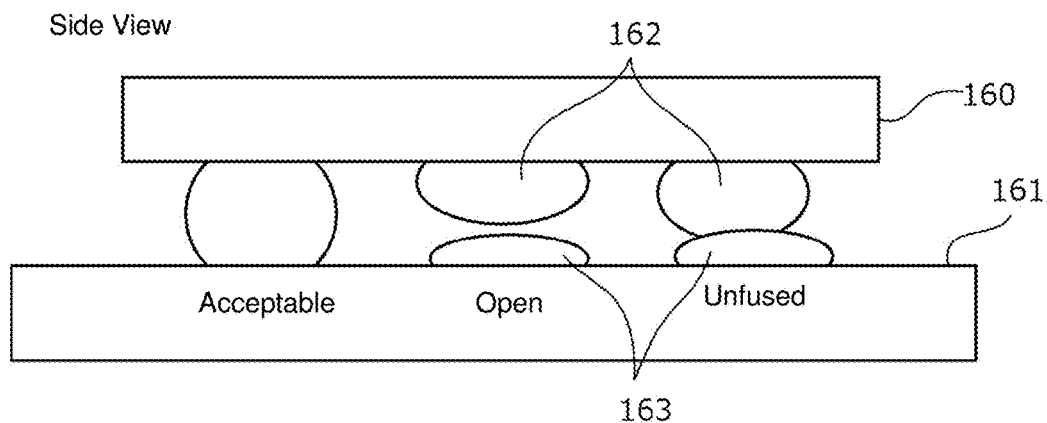
FIG. 16A is a side view of a BGA component.
Figure 16B:
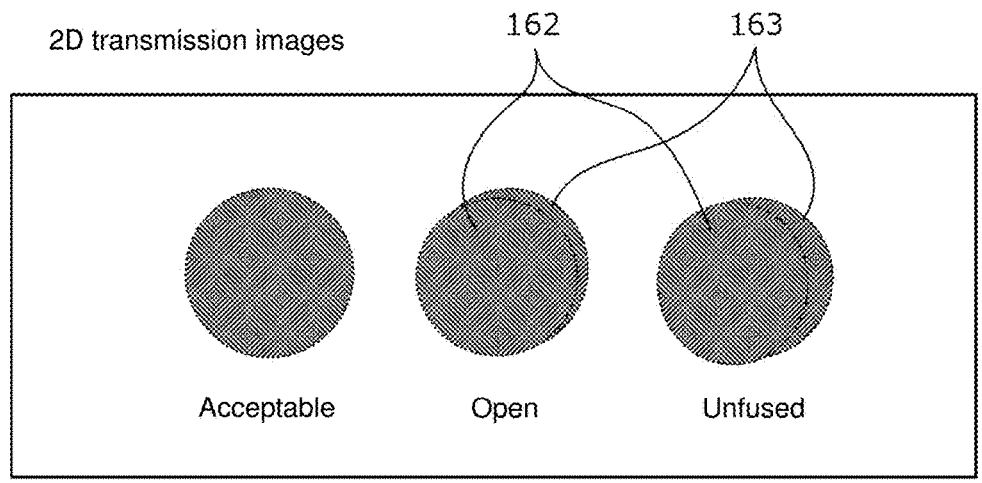
FIG. 16B is a diagram illustrating an X-ray transmission image of a BGA component.
Figure 17A:
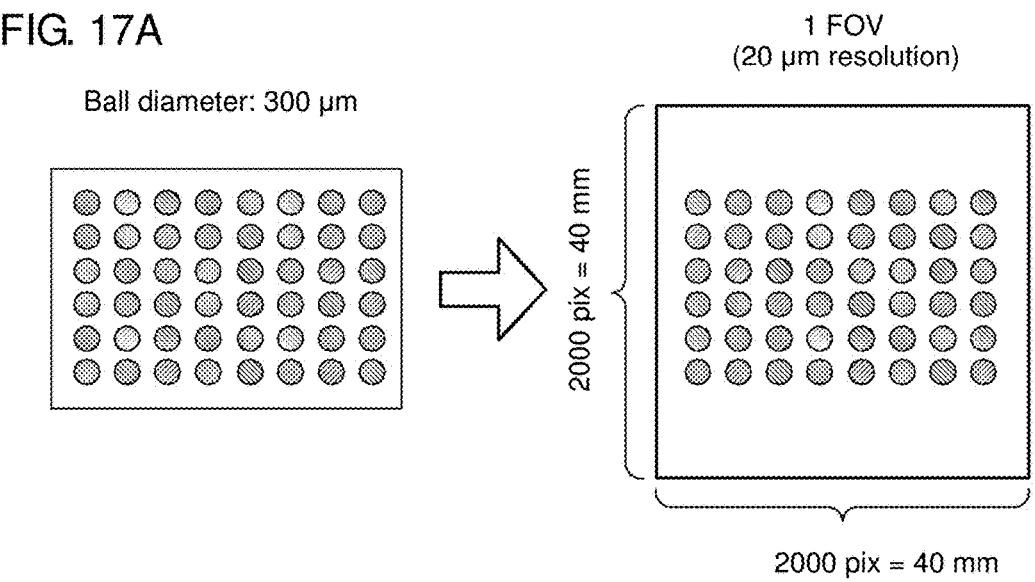
FIG. 17A is a diagram illustrating imaging of the entire component performed using a single field of view.
Figure 17B:
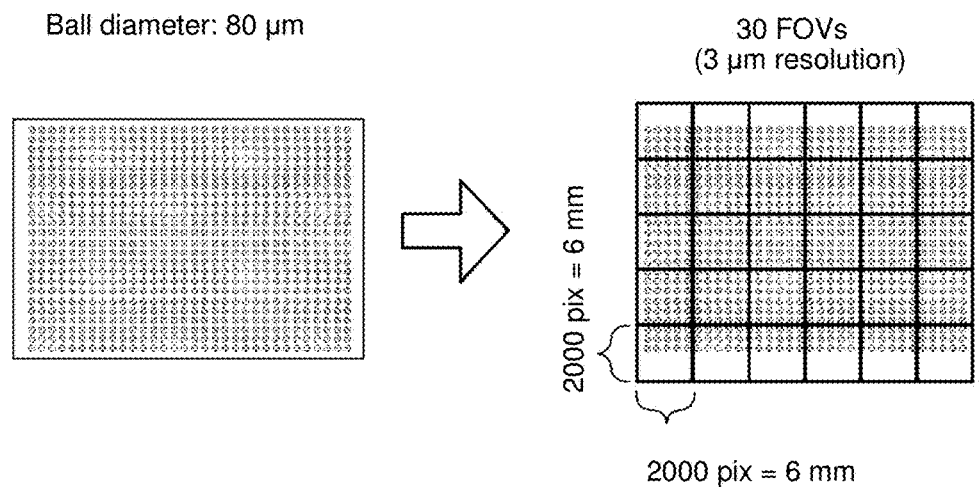
FIG. 17B is a diagram illustrating imaging of the component performed using multiple fields of view for divided areas.

FIG. 15 is a flowchart showing a bridge inspection process performed for a 2D-imaged ball in one example. First, the inspection unit 106 obtains the inter-solder distance L measured from a 2D image (step S150). When the inter-solder distance L is zero (in other words, when the inspection target 2D-imaged ball is in contact with the adjacent solder ball), the inspection unit 106 determines that the component has a bridge defect (steps S151 and S152). When the inter-solder distance L exceeds the threshold TH, the inspection unit 106 determines that the component is acceptable (step S153). The processing otherwise advances to step S154.

In step S154, the inspection unit 106 obtains the component-pad deviation of the 2D-imaged ball estimated from the 3D information. When the deviation is greater than zero, the inspection unit 106 corrects the threshold TH in accordance with the deviation (step S155). For example, a value obtained by subtracting the deviation from the threshold TH may be used as a new threshold TH. When the direction of the component-pad deviation is different from (not parallel to) the direction of the solder ball alignment, the inspection unit 106 may calculate the deviation in the direction of the solder ball alignment, and then subtract the obtained deviation from the threshold TH.

The inspection unit 106 then compares the inter-solder distance L with the corrected threshold TH (step S156). When the inter-solder distance L exceeds the corrected threshold TH, the inspection unit 106 determines that the component is acceptable (step S153), or otherwise determines that the component has a bridge defect (step S152).

5. Ball Height Inspection of 2D-Imaged Ball

The inspection unit 106 obtains the 2D-imaged ball height H in Z-direction estimated from the 3D information for the 3D-imaged ball. When the height H in Z-direction either exceeds a first threshold TH1 or is less than a second threshold TH2 (TH2<TH1), the inspection unit 106 determines that the component is defective, or otherwise (when TH2 H TH1) determines that the component is acceptable.

Advantages of Present Embodiment

The 2D/3D-combined inspection according to the present embodiment described above uses 3D imaging in a limited portion of the inspection area (3D imaging areas A1 to A5 only), and thus uses fewer imaging processes and fewer X-ray irradiations, and shortens the imaging time and the inspection time, as well as reduces the amount of radiation exposure, unlike when performing 3D imaging of the entire inspection area. The 2D/3D-combined inspection may estimate 3D information for any 2D-imaged ball included in the 2D imaging areas B1 to B15 using the 3D information extracted from the 3D images of the 3D imaging areas. Using the estimated 3D information in the 2D-imaged ball inspection, pseudo 3D inspection can be performed for the solder balls that have undergone 2D imaging alone. This allows inspection for defects that are difficult to detect in 2D inspection known in the art (e.g., a nonwetting state such as an unfused or open state, or a bridge defect).

In the present embodiment, the theoretical position of a 2D-imaged ball is determined using 3D information obtained for a 3D-imaged ball, and this theoretical position is used in the 2D-imaged ball inspection. This can yield reliable inspection results reflecting the actual state of the components (e.g., manufacturing errors or positional deviations across the entire component), thus improving the inspection accuracy and reliability.

In the present embodiment, the bridge inspection is performed based on any component-pad deviation and its deviation direction. This can yield reliable inspection results reflecting tilts in the solder balls, thus improving the inspection accuracy and reliability.

The specific structures in the embodiments described above are mere examples of the present invention. The scope of the present invention is not limited to the embodiments described above, but may be modified variously within the scope of the technical ideas of the invention. For example, 2D information measured from 2D images or 3D information measured from 3D images may be any item of image information that can be extracted from these images. Further, 3D information for 2D-imaged balls estimated from 3D information for 3D-imaged balls may be designed to be any item of information or to be estimated using any method.

REFERENCE SIGNS LIST

A1 to A5 3D imaging area (first area)
B1 to B15 2D imaging area (second area)
1 X-ray inspection apparatus
10 controller
11 stage
12 X-ray source
13 X-ray detector
14 circuit board
15 component
100 view field defining unit
101 storage unit
102 2D image generation unit
103 3D image generation unit
104 extraction unit
105 3D information estimation unit
106 inspection unit
107 result output unit
60 solder ball (inspection target)
61 pad end (first end)

62 component end (second end)
63 projected image
64 center
70a, 70b, 70c sliced position
71a, 71b, 71c sliced image
80 solder ball
81 center
82 adjacent solder ball
83 major diameter angle
160 component
161 circuit board
162 solder ball
163 solder paste piece

The invention claimed is:

1. An X-ray inspection apparatus for inspecting a workpiece including a plurality of inspection targets, the apparatus comprising:
    a 3D processing unit configured to perform 3D imaging for capturing a 3D image of a first area through multiple X-ray irradiations, the first area being a part of an inspection area defined for the workpiece;
    a 2D processing unit configured to perform 2D imaging for capturing a 2D image of a second area through a single X-ray irradiation, the second area being a part of the inspection area and being different from the first area;
    an extraction unit configured to extract 3D information for a first inspection target included in the first area from the 3D image of the first area captured through the 3D imaging, and to extract 2D information for a second inspection target included in the second area from the 2D image of the second area captured through the 2D imaging;
    a 3D information estimation unit configured to estimate 3D information for the second inspection target using the 3D information for the first inspection target extracted by the extraction unit; and
    an inspection unit configured to inspect the second inspection target using the 2D information for the second inspection target extracted by the extraction unit and the 3D information for the second inspection target estimated by the 3D information estimation unit.

2. The X-ray inspection apparatus according to claim 1, wherein
    the first area includes a plurality of first inspection targets, and
    the 3D information estimation unit calculates the 3D information for the second inspection target through interpolation or extrapolation using the 3D information for the plurality of first inspection targets.

3. The X-ray inspection apparatus according to claim 2, wherein
    when an XYZ coordinate system is defined to have an XY-plane orthogonal to a direction of X-ray irradiation in the 2D imaging,
    the extraction unit extracts an XY-position and a Z-direction height of each of the plurality of first inspection targets from the 3D image of the first area, and extracts an XY-position of the second inspection target from the 2D image of the second area, and
    the 3D information estimation unit calculates a Z-direction height of the second inspection target at the XY-position through interpolation or extrapolation using the Z-direction height of each of the plurality of first inspection targets.

4. The X-ray inspection apparatus according to claim 2, wherein
    when an XYZ coordinate system is defined to have an XY-plane orthogonal to a direction of X-ray irradiation in the 2D imaging,
    the extraction unit extracts an XY-position and volumetric information of each of the plurality of first inspection targets from the 3D image of the first area, and extracts an XY-position of the second inspection target from the 2D image of the second area, and
    the 3D information estimation unit calculates volumetric information of the second inspection target at the XY-position through interpolation or extrapolation using the volumetric information of each of the plurality of first inspection targets.

5. The X-ray inspection apparatus according to claim 2, wherein
    when an XYZ coordinate system is defined to have an XY-plane orthogonal to a direction of X-ray irradiation in the 2D imaging,
    the extraction unit extracts an XY-position of each of the plurality of first inspection targets from the 3D image of the first area, and
    the 3D information estimation unit calculates a predicted XY-positon of the second inspection target through interpolation or extrapolation using the XY-position of each of the plurality of first inspection targets.

6. The X-ray inspection apparatus according to claim 2, wherein
    when an XYZ coordinate system is defined to have an XY-plane orthogonal to a direction of X-ray irradiation in the 2D imaging, and the workpiece has a first end and a second end in Z-direction,
    the extraction unit extracts XYZ-positions of a first end and a second end of each of the plurality of first inspection targets from the 3D image of the first area,
    the 3D information estimation unit calculates a predicted XYZ-position of a first end of the second inspection target through interpolation or extrapolation using the XYZ-position of the first end of each of the plurality of first inspection targets, and calculates a predicted XYZ-position of the second end of the second inspection target through interpolation or extrapolation using the XYZ-position of the second end of each of the plurality of the first inspection targets.

7. The X-ray inspection apparatus according to claim 6, wherein
    the 3D information estimation unit calculates a deviation between the first end and the second end of the second inspection target in the XY-plane using the predicted XYZ-position of the first end and the predicted XYZ-position of the second end.

8. The X-ray inspection apparatus according to claim 6, wherein
    the 3D information estimation unit calculates a predicted XY-positon of the second inspection target by calculating an average of the predicted XYZ-position of the first end and the predicted XYZ-position of the second end.

9. The X-ray inspection apparatus according to claim 5, wherein
    the extraction unit extracts an actual XY-position of the second inspection target from the 2D image of the second area, and
    the inspection unit compares the actual XY-position of the second inspection target extracted by the extraction unit with the predicted XY-position of the second inspection target estimated by the 3D information estimation unit to determine whether the second inspection target is defective.

10. The X-ray inspection apparatus according to claim 7, wherein
the extraction unit extracts a distance between the second inspection target and an inspection target adjacent to the second inspection target from the 2D image of the second area, and
the inspection unit determines whether the second inspection target is defective using the distance extracted by the extraction unit and the deviation between the first end and the second end of the second inspection target in the XY-plane estimated by the 3D information estimation unit.

11. The X-ray inspection apparatus according to claim 7, wherein
the extraction unit extracts an actual circularity of the second inspection target from the 2D image of the second area, and
the inspection unit estimates a circularity of the second inspection target using the deviation between the first end and the second end of the second inspection target in the XY-plane, and compares the estimated circularity with the actual circularity of the second inspection target extracted by the extraction unit to determine whether the second inspection target is defective.

12. The X-ray inspection apparatus according to claim 2, wherein
when an XYZ coordinate system is defined to have an XY-plane orthogonal to a direction of X-ray irradiation in the 2D imaging,
the extraction unit extracts an XY-position, a Z-direction height, and volumetric information of each of the plurality of first inspection targets from the 3D image of the first area, and extracts an XY-position and a surface area of the second inspection target from the 2D image of the second area,
the 3D information estimation unit calculates a Z-direction height and volumetric information of the second inspection target at the XY-position through interpolation or extrapolation using the Z-direction height and the volumetric information of each of the plurality of first inspection targets, and the inspection unit compares the volumetric information of the second inspection target calculated from the surface area of the second inspection target extracted by the extraction unit and the Z-direction height of the second inspection target estimated by the 3D information estimation unit with the volumetric information of the second inspection target estimated by the 3D information estimation unit to determine whether the second inspection target is defective.

13. The X-ray inspection apparatus according to claim 1, wherein
the workpiece is an electronic component, and each inspection target is a solder piece for joining the electronic component and a circuit board.

14. A method for controlling an X-ray inspection apparatus that inspects a workpiece including a plurality of inspection targets using X-rays, the method comprising:
performing 3D imaging for capturing a 3D image of a first area through multiple X-ray irradiations, the first area being a part of an inspection area defined for the workpiece;
performing 2D imaging for capturing a 2D image of a second area through a single X-ray irradiation, the second area being a part of the inspection area and being different from the first area;
extracting 3D information for a first inspection target included in the first area from the 3D image of the first area captured through the 3D imaging; and
extracting 2D information for a second inspection target included in the second area from the 2D image of the second area captured through the 2D imaging;
estimating 3D information for the second inspection target using the extracted 3D information for the first inspection target; and
inspecting the second inspection target using the extracted 2D information for the second inspection target and the estimated 3D information for the second inspection target.

15. A non-transitory computer-readable recording medium storing a program causing a processor included in an X-ray inspection apparatus to implement the method for controlling an X-ray inspection apparatus according to claim 14.

* * * * *